United States Patent
Mistry

(10) Patent No.: US 12,059,354 B2
(45) Date of Patent: Aug. 13, 2024

(54) ROBOTIC ACETABULUM PREPARATION FOR ACCEPTANCE OF ACETABULAR CUP WITH ENGAGEMENT FEATURES

(71) Applicant: Howmedica Osteonics Corp., Mahwah, NJ (US)

(72) Inventor: Amit Mistry, Weston, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 430 days.

(21) Appl. No.: 16/788,702

(22) Filed: Feb. 12, 2020

(65) Prior Publication Data
US 2020/0261232 A1 Aug. 20, 2020

Related U.S. Application Data

(60) Provisional application No. 62/806,297, filed on Feb. 15, 2019.

(51) Int. Cl.
*A61F 2/34* (2006.01)

(52) U.S. Cl.
CPC ........ *A61F 2/34* (2013.01); *A61F 2002/3412* (2013.01)

(58) Field of Classification Search
CPC ............... A61F 2/34; A61F 2002/3412; A61F 2002/30878; A61F 2002/30879; A61F 2002/30891; A61F 2002/3403; A61F 2/4609; A61F 2/30771; A61F 2002/3417; A61F 2002/349; A61F 2002/342; A61F 2002/3425; A61F 2002/343
See application file for complete search history.

(56) References Cited

U.S. PATENT DOCUMENTS

| | | | | |
|---|---|---|---|---|
| 3,698,017 A | * | 10/1972 | Scales | A61F 2/34 623/22.24 |
| 3,781,918 A | * | 1/1974 | Mathys | A61F 2/34 623/23.43 |
| 3,829,904 A | * | 8/1974 | Ling | A61B 90/39 623/22.39 |
| 3,840,904 A | * | 10/1974 | Tronzo | A61F 2/34 623/22.32 |

(Continued)

OTHER PUBLICATIONS

ADM® X3® Mobile Bearing Hip® System Surgical Protocol, Stryker Corporation, Copyright © 2013 Stryker, 24 pages.

(Continued)

*Primary Examiner* — Brian A Dukert
*Assistant Examiner* — Melissa A Hoban
(74) *Attorney, Agent, or Firm* — Lerner David LLP

(57) ABSTRACT

In one embodiment, the present disclosure relates to an acetabular cup for implantation into a prepared acetabulum. The acetabular cup includes an inner surface, an outer surface, and an end face that separates the inner surface and the outer surface. The end face is opposite a polar region of the acetabular cup and circumscribes an open end of the acetabular cup. A plurality of protrusions project outwardly from the outer surface at predefined locations. The acetabular cup is operatively engaged to the prepared acetabulum in a planned orientation when the plurality of protrusions are received in corresponding predefined recesses in the prepared acetabulum.

13 Claims, 12 Drawing Sheets

(56) References Cited

U.S. PATENT DOCUMENTS

| | | | | |
|---|---|---|---|---|
| 4,231,120 A * | 11/1980 | Day | A61F 2/3662 | 433/173 |
| 4,271,849 A * | 6/1981 | Rehder | A61F 2/3603 | 606/81 |
| 4,437,193 A * | 3/1984 | Oh | A61F 2/34 | 623/22.24 |
| 4,566,138 A * | 1/1986 | Lewis | A61F 2/34 | 606/92 |
| 4,650,491 A * | 3/1987 | Parchinski | A61F 2/34 | 403/140 |
| 4,664,668 A * | 5/1987 | Beck | A61F 2/30771 | 623/23.29 |
| 4,715,859 A * | 12/1987 | Schelhas | A61F 2/34 | 623/22.27 |
| 4,795,469 A * | 1/1989 | Oh | A61F 2/4637 | 623/22.27 |
| 4,795,470 A * | 1/1989 | Goymann | A61F 2/30771 | 623/22.24 |
| 4,863,538 A * | 9/1989 | Deckard | B22F 3/105 | 264/642 |
| 4,883,491 A * | 11/1989 | Mallory | A61F 2/30734 | 623/22.27 |
| 4,919,676 A * | 4/1990 | Zweymuller | A61F 2/34 | 623/22.31 |
| 4,944,817 A * | 7/1990 | Bourell | B23K 26/08 | 264/642 |
| 4,997,447 A * | 3/1991 | Shelley | A61F 2/34 | 623/22.31 |
| 5,017,753 A * | 5/1991 | Deckard | B22F 10/20 | 219/121.84 |
| 5,076,869 A * | 12/1991 | Bourell | B29C 64/153 | 219/121.85 |
| 5,358,532 A * | 10/1994 | Evans | A61F 2/34 | 623/22.23 |
| 5,405,402 A * | 4/1995 | Dye | A61F 2/30724 | 623/22.38 |
| 5,443,519 A * | 8/1995 | Averill | A61F 2/34 | 623/22.37 |
| 5,458,649 A * | 10/1995 | Spotorno | A61F 2/34 | 623/22.27 |
| 5,480,448 A * | 1/1996 | Mikhail | A61F 2/4637 | 623/22.24 |
| 5,571,201 A * | 11/1996 | Averill | A61F 2/34 | 606/86 R |
| 5,645,601 A * | 7/1997 | Pope | A61F 2/32 | 623/23.39 |
| 5,658,346 A * | 8/1997 | Willi | A61F 2/34 | 623/22.24 |
| 5,702,477 A * | 12/1997 | Capello | A61F 2/30724 | 623/22.21 |
| 5,702,478 A * | 12/1997 | Tornier | A61F 2/30724 | 623/22.24 |
| 5,725,593 A * | 3/1998 | Caracciolo | A61F 2/32 | 623/22.23 |
| 5,931,870 A * | 8/1999 | Cuckler | A61F 2/34 | 623/22.21 |
| 6,136,034 A * | 10/2000 | Townley | A61F 2/30771 | 623/22.11 |
| 6,290,727 B1 * | 9/2001 | Otto | A61F 2/30724 | 623/22.21 |
| 6,398,815 B1 * | 6/2002 | Pope | A61F 2/32 | 623/18.11 |
| 7,402,177 B2 * | 7/2008 | Jones | A61F 2/30724 | 623/22.32 |
| 7,513,913 B2 * | 4/2009 | Hoermansdoerfer | A61F 2/34 | 623/22.31 |
| 7,537,664 B2 * | 5/2009 | O'Neill | B22F 10/28 | 148/516 |
| 7,572,295 B2 * | 8/2009 | Steinberg | A61B 17/1666 | 623/22.32 |
| 7,758,653 B2 * | 7/2010 | Steinberg | A61C 8/00 | 623/23.5 |
| 7,780,740 B2 * | 8/2010 | Steinberg | A61F 2/30756 | 623/22.21 |
| 7,831,292 B2 * | 11/2010 | Quaid | A61B 34/37 | 345/157 |
| 8,268,099 B2 | 9/2012 | O'Neill et al. | | |
| 8,268,100 B2 | 9/2012 | O'Neill et al. | | |
| 8,535,385 B2 * | 9/2013 | Hanssen | A61F 2/30734 | 623/23.19 |
| 8,556,981 B2 * | 10/2013 | Jones | A61F 2/30 | 623/21.16 |
| 8,617,171 B2 * | 12/2013 | Park | G06K 9/6201 | 606/88 |
| 8,728,387 B2 | 5/2014 | Jones et al. | | |
| 8,992,703 B2 | 3/2015 | O'Neill et al. | | |
| 9,456,901 B2 | 10/2016 | Jones et al. | | |
| 9,907,661 B2 * | 3/2018 | Ries | A61F 2/34 | |
| 2005/0085915 A1 * | 4/2005 | Steinberg | A61B 17/1684 | 623/23.72 |
| 2005/0202371 A1 * | 9/2005 | McGuire | A61F 2/30767 | 623/20.15 |
| 2006/0142657 A1 * | 6/2006 | Quaid | A61B 17/1703 | 600/424 |
| 2006/0147332 A1 * | 7/2006 | Jones | B23K 26/342 | 148/513 |
| 2006/0235536 A1 * | 10/2006 | Baliktay | A61L 27/06 | 623/18.11 |
| 2006/0241781 A1 * | 10/2006 | Brown | A61F 2/34 | 623/22.32 |
| 2007/0142922 A1 * | 6/2007 | Lewis | A61F 2/30721 | 623/22.36 |
| 2008/0009953 A1 * | 1/2008 | Ling | A61F 2/4684 | 623/22.21 |
| 2008/0025817 A1 * | 1/2008 | Hormansdorfer | A61F 2/34 | 623/22.21 |
| 2009/0216325 A1 * | 8/2009 | May | A61F 2/389 | 606/300 |
| 2011/0190901 A1 * | 8/2011 | Weissberg | A61F 2/34 | 623/22.24 |
| 2011/0264231 A1 * | 10/2011 | Theillez | A61F 2/34 | 623/22.32 |
| 2013/0035766 A1 * | 2/2013 | Meridew | A61F 2/34 | 623/22.21 |
| 2013/0131741 A1 * | 5/2013 | Kourtis | A61F 2/0095 | 606/86 R |
| 2014/0052149 A1 * | 2/2014 | van der Walt | A61B 34/20 | 606/130 |
| 2014/0188132 A1 * | 7/2014 | Kang | A61B 34/30 | 606/130 |
| 2014/0246943 A1 * | 9/2014 | Omekanda | H02K 17/205 | 310/211 |
| 2015/0080717 A1 * | 3/2015 | Ferko | A61F 2/38 | 600/425 |
| 2015/0119987 A1 * | 4/2015 | Davignon | G16H 50/50 | 703/1 |
| 2015/0258735 A1 | 9/2015 | O'Neill et al. | | |
| 2017/0000562 A1 * | 1/2017 | Frank | A61B 17/80 | |
| 2017/0014235 A1 | 1/2017 | Jones et al. | | |
| 2017/0181755 A1 * | 6/2017 | Librot | A61B 34/10 | |
| 2018/0055641 A1 | 3/2018 | Jones et al. | | |
| 2019/0021796 A1 * | 1/2019 | Timperley | A61B 34/30 | |
| 2020/0261232 A1 * | 8/2020 | Mistry | A61F 2/30771 | |

OTHER PUBLICATIONS

Trident® II Tritanium® Acetabular Ssystem Surgical Protocol, Howmedica Osteonics Corp., Copyright © 2018 Stryker, 32 pages.

* cited by examiner

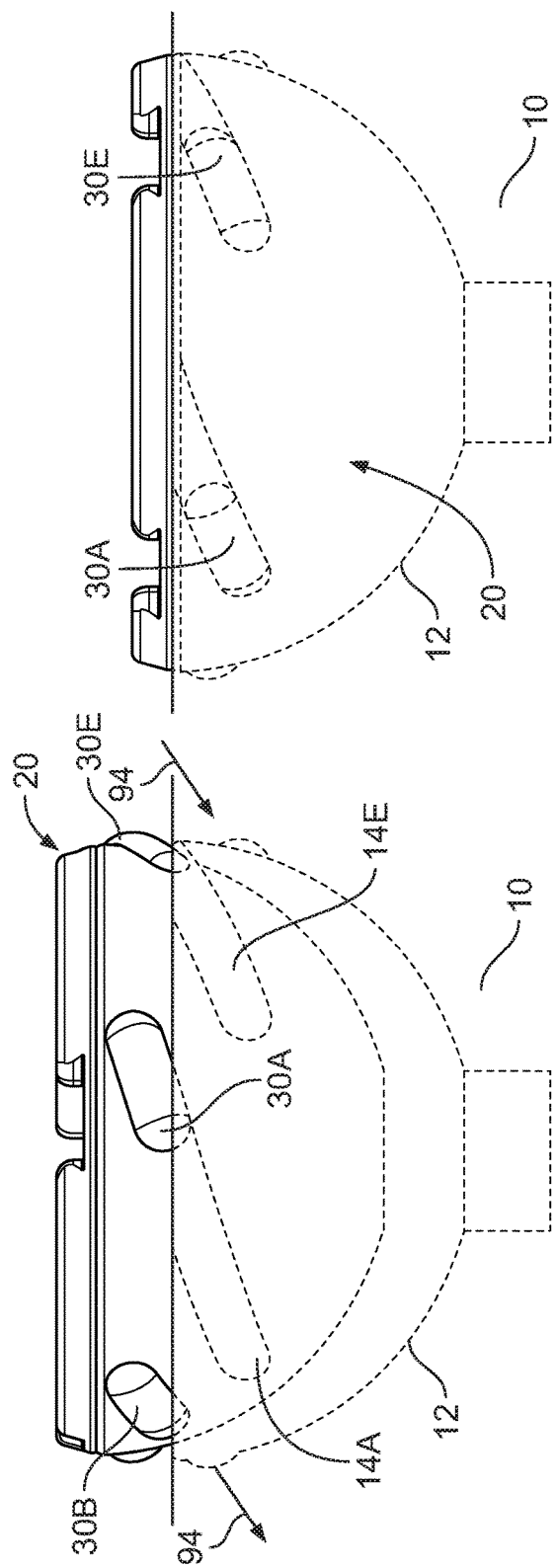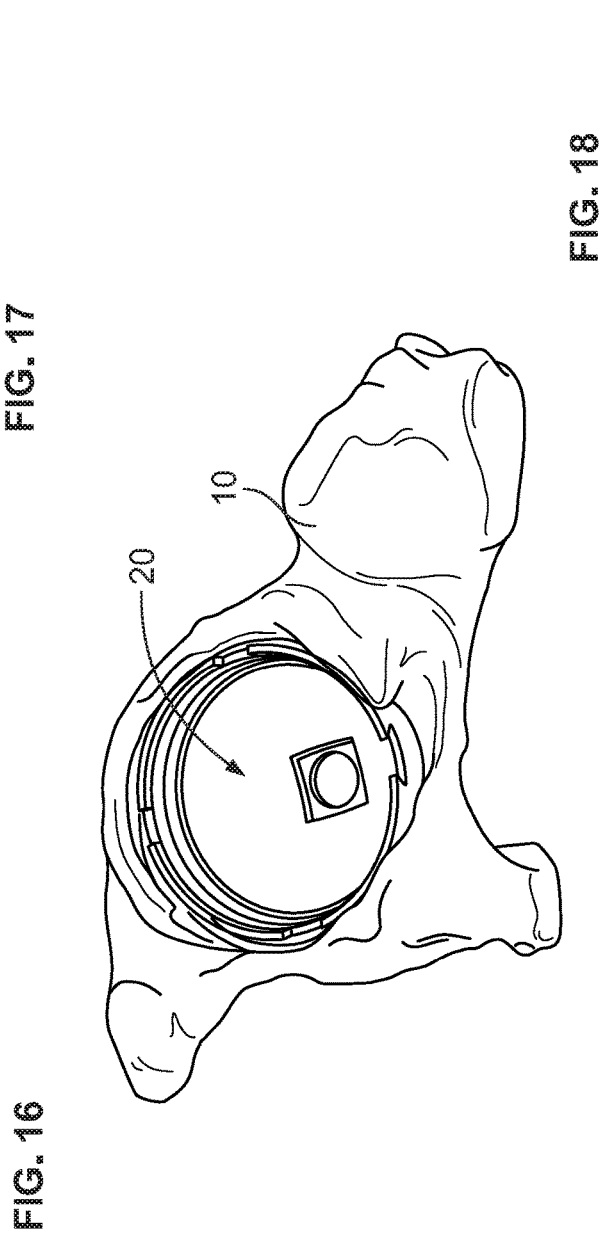

ROBOTIC ACETABULUM PREPARATION FOR ACCEPTANCE OF ACETABULAR CUP WITH ENGAGEMENT FEATURES

CROSS-REFERENCE TO RELATED APPLICATION

This application claims the benefit of the filing date of U.S. Provisional Patent Application No. 62/806,297, filed Feb. 15, 2019, the disclosure of which is hereby incorporated by reference herein in its entirety.

BACKGROUND OF THE INVENTION

To complete a hip surgery, an acetabular cup must be fixed into place within an acetabular cavity. In one procedure, an acetabulum is resurfaced through the operation of a tool with an attached reamer basket, the initial reamer basket being replaced with larger reamer baskets in a sequence to complete the procedure. The resurfacing is performed to prepare the acetabulum for the placement of an acetabular cup. Because the baskets are often swapped multiple times before the surface is finished, the resultant cavity is typically not hemispherical and instead is eccentric relative to a shape of the cup. One reason for this is the difficulty that a surgeon encounters maintaining the tool in a desired position while reaming into the bone to reshape the cavity for cup placement. Further, the need to swap reamer baskets in a single procedure renders the possibility of an accurate resection even less likely. Because of the resultant shape of the cavity, an implanted cup will often only engage the bone near a rim at an upper end of the cavity, leaving voids between the cup and bone. Such conditions may result in misalignment of a seated acetabular cup.

Some existing approaches to seat acetabular cups involve under reaming the bone by one cup size. Then, the cup may be impacted into the cavity by force through a press fit. Because the cavity is smaller than the cup, the rationale is that the cup will have continuous fixation with the bone around at least its outer rim perimeter. However, after initial fixation of the cup into the bone, it becomes difficult to advance the cup further into the cavity. Accordingly, there is a risk that a gap will exist between portions of the cup and the acetabular bone surface that defines the cavity. These conditions are undesirable because there is an increased risk that the cup may loosen and that the cup may never be fully fixed to the bone. Other remedial measures may further complicate the surgery, such as the insertion of fasteners through the cup to promote its fixation to the bone.

The above approaches are also performed using robotics. However, even with robotics the use of a series of reaming baskets is required to prepare the acetabular cavity. Moreover, even with robotics there is still a need for impaction of the acetabular cup to fix it into place. Indeed, these steps continue to require significant surgeon involvement. Additionally, the laborious nature of existing techniques including reaming and impaction procedures can cause injury to the surgeons themselves over time.

Thus, a need exists for a surgical technique and associated implant designs to improve the effectiveness of procedures to seat implants in the joint including improved accuracy and stability of implant placement.

BRIEF SUMMARY OF THE INVENTION

In one aspect, the present disclosure relates to an acetabular cup. In one embodiment, an acetabular cup includes an inner surface, an outer surface with a plurality of protrusions thereon and an end face. The end face separates the inner surface and the outer surface and is opposite a polar region of the cup. The end face circumscribes an open end of the cup. Each of the plurality of protrusions has a long dimension that is oriented at an acute angle relative to an axis passing through a center of the polar region of the cup and a center of the open end of the cup. An end of the long dimension is tapered.

In some embodiments, the taper of each of the plurality of protrusions may be at a leading end of the long dimension, the leading end located further from the end face than other locations on the protrusion. In some embodiments, each of the plurality of protrusions may include flat, convex, or a combination of flat and convex surfaces. In some embodiments, one or more of the plurality of protrusions may consist of flat, convex, or a combination of flat and convex surfaces. In some embodiments, the plurality of protrusions may include first, second and third protrusions each located at a first distance from the end face and equally spaced around a perimeter of the outer surface at the first distance. In some embodiments, each of the plurality of protrusions may have an oblong shape of a first size. In some embodiments, each of the plurality of protrusions may be oriented at a first angle relative to the axis. In some embodiments, the first angle may range from 65 to 75 degrees.

In some embodiments, each of the plurality of protrusions may be symmetrical about the long dimension. In some embodiments, the long dimension of each of the plurality of protrusions may extend between a leading end and a trailing end, the leading end and the trailing end both being defined by a rounded taper. In some embodiments, the end of the long dimension of each of the plurality of protrusions may be a leading end and the long dimension may extend between the leading end and a trailing end, a width of the protrusion tapering continuously from the trailing end to the leading end. In some embodiments, each of the plurality of protrusions may include a pair of spherical caps abutting one another such that the long dimension is measured between centers of the respective spherical caps. In some embodiments, each of the plurality of protrusions may be attached to the cup, the cup being formed prior to the attachment of the plurality of protrusions to the cup.

In one embodiment, an acetabular cup includes an inner surface, an outer surface with three protrusions thereon and an end face separating the inner surface and the outer surface, the end face opposite a polar region of the cup. Each of the three protrusions includes two ends. Each of the two ends is located at a first distance from the end face and a midpoint between the two ends is located at a second distance from the end face, the first distance being less than the second distance.

In some embodiments, each of the protrusions may be U-shaped and oriented so that a curved bottom of the U-shape is located toward the polar region while ends of the U-shape are located toward the end face. In some embodiments, each of the three protrusions may include a convex surface. In some embodiments, the three protrusions may be equally spaced around a perimeter of the outer surface and located at a first distance from the end face.

In one embodiment, an acetabular cup includes an inner surface, an outer surface with a protrusion thereon and an end face separating the inner surface and the outer surface, the end face opposite a polar region of the cup. The protrusion forms a closed perimeter on the outer surface and is located at a first distance from a center of the polar region of the cup at a first location and at a second distance from the center at a second location, the first distance being different from the second distance.

In some embodiments, the protrusion may form a pattern that is symmetrical about an axis. In some embodiments, the protrusion may have a length concomitant with the perimeter that includes a repeating pattern of a first linear portion, a first ninety degree bend, a second linear portion, a second ninety degree bend in a direction opposite the first, a third linear portion, and a third ninety degree bend in the same direction as the second ninety degree bend. In some embodiments, the perimeter of the protrusion may be circular. In some embodiments, the protrusion may include a plurality of extensions extending toward the polar region from the closed perimeter. In some embodiments, the protrusion may have a length concomitant with the perimeter and the length is defined by a repeating pattern of a trough with an upper apex representing a first location on the protrusion closest to the center of the polar region and an outward curve with a lower apex representing a second location on the protrusion that is furthest from the center of the polar region. The entirety of the length may include three upper apices and three lower apices. In some embodiments, the protrusion may extend around the perimeter in a wave pattern with a first plurality of apices closest to the center of the polar region and a second plurality of apices furthest from the center of the polar region. Each of the first plurality of apices may be at a first distance from the center and each of the second plurality of apices may be at a second distance from the center.

In one embodiment, an acetabular cup, configured for implantation into a prepared acetabulum, includes an inner surface, an outer surface and an end face that separates the inner surface and the outer surface. The end face is opposite a polar region of the acetabular cup and circumscribes an open end of the cup. The outer surface includes a plurality of protrusions that project outward from a remainder of the outer surface. The plurality of projections are located at predefined locations on the outer surface. The acetabular cup is adapted so that when the plurality of protrusions are received in corresponding predefined recesses in the prepared acetabulum, the acetabular cup is operatively engaged to the prepared acetabulum in a planned orientation.

In some embodiments, the corresponding predefined recesses may have a volume that is substantially the same as a volume of the plurality of protrusions. In some embodiments, the corresponding predefined recesses may have an initial volume less than a volume of the plurality of protrusions. In some embodiments, the plurality of protrusions may be configured to snap-fit into the corresponding predefined recesses. In some embodiments, upon rotation of the plurality of protrusions about a polar axis of the cup, the plurality of protrusions may be configured to rotate into engagement with the corresponding predefined recesses. In some embodiments, each of the plurality of protrusions may have a long dimension that is oriented at an acute angle relative to an axis passing through a center of the polar region of the cup and a center of the open end of the cup. An end of the long dimension may be tapered. In some embodiments, the end face of the acetabular cup may be non-planar. In some embodiments, the non-planar end face may have alternating peaks and valleys.

In one embodiment, an acetabular cup includes an inner surface, an outer surface and an end face separating the inner surface and the outer surface. The end face is opposite a polar region of the cup and circumscribes an open end of the cup. A plurality of protrusions are located on the outer surface. Each protrusion of the plurality of protrusions has a long dimension that is oriented at an acute angle relative to an axis passing through a center of the polar region and a center of the open end of the acetabular cup. An end of the long dimension is tapered. The plurality of protrusions are sized to engage with complementary surfaces in a prepared acetabulum.

In some embodiments, the taper of each of the plurality of protrusions may be at a leading end of the long dimension, the leading end located further from the end face than other locations on the protrusion. In some embodiments, each of the plurality of protrusions may include flat, convex, or a combination of flat and convex surfaces. In some embodiments, the plurality of protrusions may include first, second and third protrusions each located at a first distance from the end face and equally spaced around a perimeter of the outer surface at the first distance. In some embodiments, the long dimension of each of the plurality of protrusions may extend between a leading end and a trailing end, the leading end and the trailing end both being defined by a rounded taper. In some embodiments, the end of the long dimension of each of the plurality of protrusions may be a leading end and the long dimension may extend between the leading end and a trailing end, a width of the protrusion tapering continuously from the trailing end to the leading end.

In one embodiment, an acetabular cup includes an inner surface, an outer surface, and an end face that separates the inner surface and the outer surface. The end face is opposite a polar region of the acetabular cup. A protrusion is located on the outer surface. The protrusion includes a continuous segment with a length that extends from a first location to a third location with a second location in between. The first location and the third location are at a first distance from a center of the polar region of the acetabular cup while the second location is at a second distance from the center of the polar region. The first distance is different from the second distance. The protrusion is operatively engaged to a prepared acetabulum when the protrusion is received in a corresponding predefined recess in the prepared acetabulum.

In some embodiments, the protrusion may have a uniform cross-sectional shape along the length of the continuous segment. In some embodiments, the protrusion may form a closed perimeter on the outer surface. In some embodiments, the protrusion may have a length concomitant with the perimeter that includes a repeating pattern of a first linear portion, a first ninety degree bend, a second linear portion, a second ninety degree bend in a direction opposite the first, a third linear portion, and a third ninety degree bend in the same direction as the second ninety degree bend. In some embodiments, the protrusion may extend around the perimeter in a wave pattern with a first plurality of apices closest to the center of the polar region and a second plurality of apices furthest from the center of the polar region. Each of the first plurality of apices may be at a first distance from the center and each of the second plurality of apices may be at a second distance from the center. In some embodiments, the protrusion may be U-shaped and oriented so that a curved bottom of the U-shape is located toward the polar region while ends of the U-shape are located toward the end face. In some embodiments, the protrusion may include a convex surface.

In another aspect, the present disclosure relates to a method of inserting an acetabular cup into an acetabulum. In one embodiment, the method includes: forming a groove in a surface of the acetabulum to prepare the acetabulum, wherein the groove, when formed, has a length from a first location at a first distance from a center of a polar region of the acetabulum to a second location at a second distance from the center, the first distance being greater than the second distance; and rotating an acetabular cup within the prepared acetabulum so that a protrusion on an outer surface of the acetabular cup engages the groove, the protrusion moving closer to the center as the acetabular cup is rotated.

In some embodiments, the rotating step may continue until the protrusion abuts an end of the at least one groove at the second location. In some embodiments, the method may include a step of positioning the acetabular cup prior to the rotating step such that a leading end of the protrusion is aligned with an end of the at least one groove located at an upper edge of the acetabulum. In some embodiments, the rotating step may include advancing a leading end of the protrusion into the at least one groove, the leading end tapered thereby reducing resistance to the rotating motion.

In some embodiments, the forming step may include forming a second groove in the surface, the second groove having a length from a third location at the first distance from the center to a fourth location at the second distance from the center. In some embodiments, the rotating step may include rotating the acetabular cup within the prepared acetabulum so that the protrusion and a second protrusion on the outer surface of the acetabular cup engage the groove and the second groove, respectively. In some embodiments, during rotation of the acetabular cup, the protrusion and the second protrusion may reach the second location of the groove and the fourth location of the second groove, respectively, at a single point in time. In some embodiments, forming the groove in the surface of the acetabulum may occur by burring the groove using a bur tool controlled by a robotic manipulator. In some embodiments, forming the groove in the surface of the acetabulum may occur by burring the groove using a bur tool and utilizing haptics so that feedback is generated if the formation in the surface occurs proximal to a boundary of a predetermined path of resection. In some embodiments, rotating the acetabular cup within the prepared acetabulum may occur by rotating the acetabular cup with a rotatable driver controlled by a robotic manipulator.

In another aspect, the present disclosure relates to a surgical system. In one embodiment, a surgical system for inserting an acetabular cup into an acetabulum of a patient includes a robotic manipulator, a navigation system and a controller. The robotic manipulator includes a plurality of links and is operable with a bur tool and a rotatable driver. The navigation system is configured to track the patient. The controller is coupled to the robotic manipulator and the navigation system and is configured to control operation of the bur tool and the rotatable driver. The controller controls operation of the bur tool to form a groove in a surface of the acetabulum to prepare the acetabulum. The groove, when formed, has a length from a first location at a first distance from a center of a polar region of the acetabulum to a second location at a second distance from the center, the first distance being greater than the second distance. The controller controls operation of the rotatable driver to rotate an acetabular cup within the prepared acetabulum so that a protrusion on an outer surface of the acetabular cup engages the groove. The protrusion moves closer to the center while engaged with the groove as the acetabular cup is rotated.

In some embodiments, the controller may be configured to control the bur tool to form a plurality of grooves such that each of the plurality of grooves has the same shape.

In one embodiment, a method includes rotating an acetabular cup about its center axis into an acetabulum such that protrusions on an outer surface of the acetabular cup precisely align with prepared bone surface features in the acetabulum. The alignment realized ensures that the protrusions adequately engage with bone upon rotation of the acetabular cup into the acetabulum.

In some embodiments, the rotating step may be preceded by one or more surgical planning steps.

BRIEF DESCRIPTION OF THE DRAWINGS

The present disclosure will be better understood on reading the following detailed description of non-limiting embodiments thereof, and on examining the accompanying drawings, in which:

FIGS. 14-18 illustrate steps in a method of implanting an acetabular cup into an acetabulum of a patient according to one embodiment of the disclosure.

DETAILED DESCRIPTION

Figure 1:
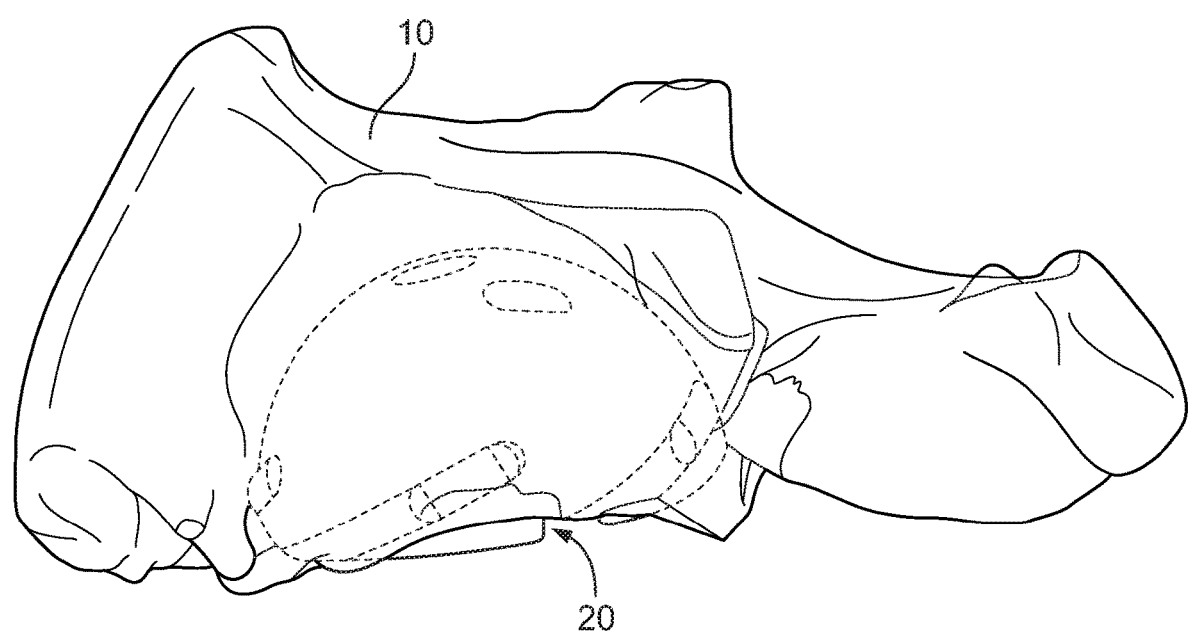
FIG. 1 is a perspective view of an acetabular cup implanted in a mammalian acetabulum according to one embodiment of the disclosure.

The present disclosure relates to devices, kits and methods directed to implants used in mammalian joints, such as acetabular implants. Throughout the disclosure, reference is made to an acetabular cup. The acetabular cup as described is an outermost acetabular implant component intended to abut a bone surface of a patient. Those skilled in the art may also know certain acetabular cups to be total hip arthroplasty ("THA") cups or adaptive dual mobility ("ADM") cups. The acetabular cup is a component of a hip implant that is fixed to an inner surface within a cavity of an acetabulum in a mammalian patient, as shown in FIG. 1 for example, where numeral 20 indicates the acetabular cup while numeral 10 indicates the pelvic bone. Although the aspects and embodiments of the disclosure are described with specific application to the hip, it is contemplated that the principles outlined herein may be employed in other areas of the body, particularly those where a close fit is desirable or required between an implant and a curved bone surface, such as other ball and socket joints. Such alternative applications include an implant for the glenoid of the shoulder, for example.

Figure 2:
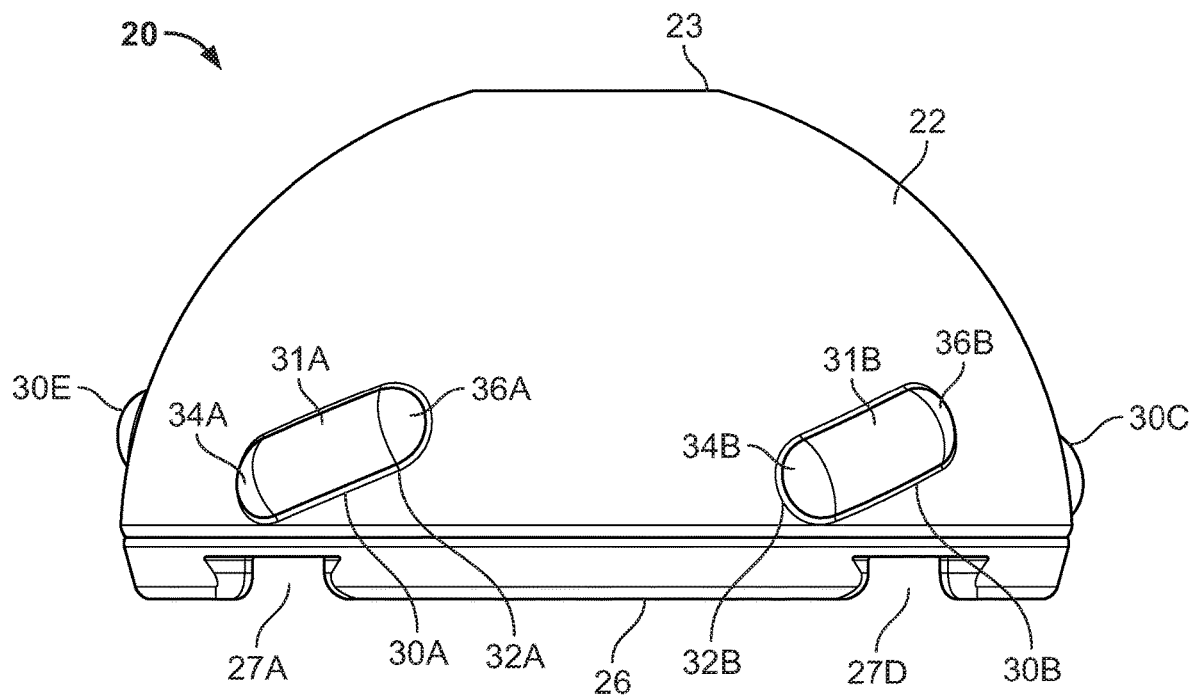
FIG. 2 is a side view of the acetabular cup shown in FIG. 1.
Figure 3:
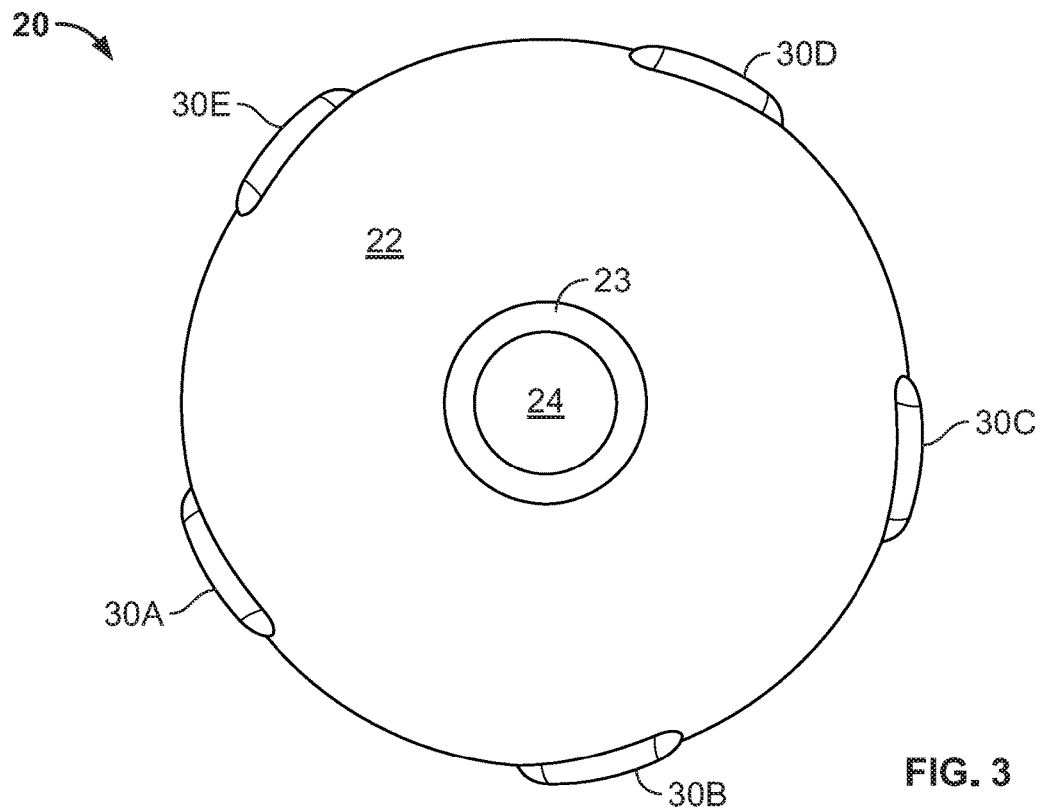
FIG. 3 is a bottom view of the acetabular cup shown in FIG. 1.

In one aspect, the present disclosure relates to an acetabular cup structure, one embodiment of which is acetabular cup 20, a THA cup, shown in FIGS. 2 and 3. Acetabular cup 20 includes a polar region with a lower rim surface 23 that extends circumferentially around opening 24 centered on a polar axis of cup 20. Opposite the polar region is an equatorial region including an upper rim surface 26 that also extends circumferentially around a volume defined by an inner surface (not shown) of cup 20.

An outer surface 22 extends from opening 24 to upper rim surface 26. Disposed on outer surface 22 are a plurality of protrusions 30A-E. Not including protrusions 30A-E, outer surface 22 has a generally hemispherical shape, although a particular shape of the outer surface may vary to suit particular anatomy. As shown in FIG. 3, each protrusion 30A-E is equally spaced around a perimeter of cup 20 and, as shown in FIG. 1, each protrusion is located at a single distance from upper rim surface 26. In acetabular cup 20, each protrusion 30A-E has the same size and shape.

Figure 14:
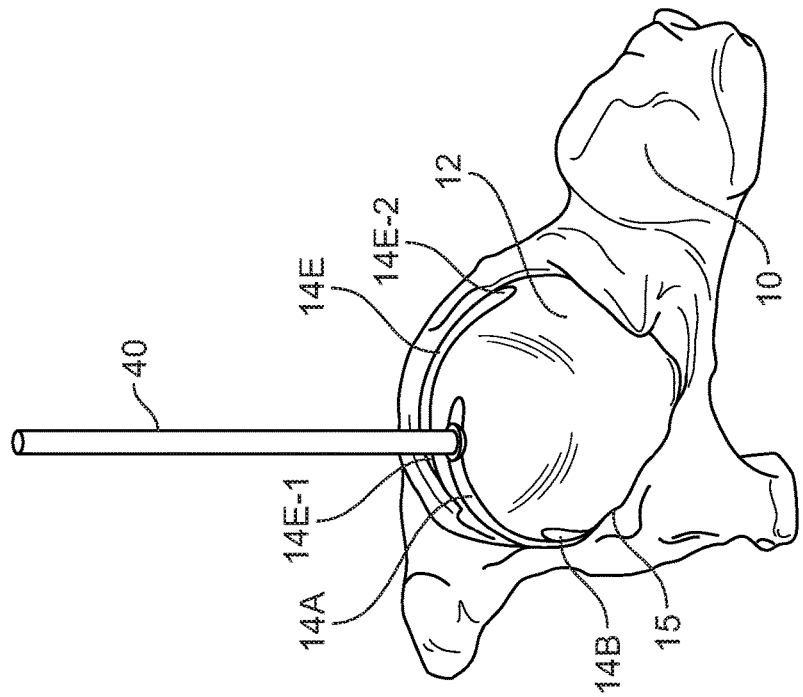
Figure 20:
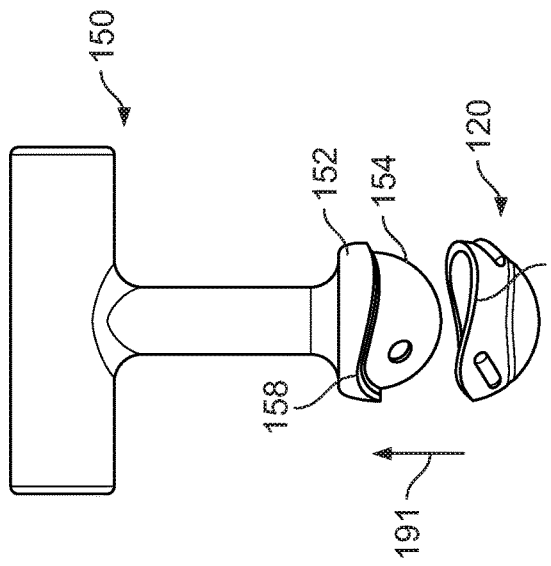
FIGS. 19-23 illustrate steps in a method of implanting an acetabular cup into an acetabulum of a patient according to one embodiment of the disclosure.

The position and orientation of each protrusion 30A-E and/or corresponding recesses or resections as shown in FIG. 14, for example, in the acetabulum can be preoperatively designed. In one aspect, the design includes a computer tomography ("CT") scan or magnetic resonance imaging ("MRI") of pelvic bone 10, for example. Other means known in the art may be used to obtain information relating to the structure of the hip joint, including pelvic bone 10. Data obtained from the CT scan or MRI is preferably converted to a working computer aided design ("CAD") model or virtual model of the patient's joint. The conversion of the data obtained from the CT scan or MRI to a working CAD model may be done in any known manner in the art. After the CAD or virtual model of the patient's joint is created, the topography or outer surface of the bones in the joint may be visualized on a computer screen or any like visual medium. Preferably, the virtual model of the patient's joint is a three-dimensional model that may be rotated and manipulated in three-dimensions such that an operator visualizing the model on a computer screen may be able to see certain tissue structures and structures of bones individually or of all the bones in a joint at once, such as the pelvis and proximal femur in THA, for example.

The design of recesses or resections in the acetabulum can be made so that acetabular cup 20 can either be rotated as shown in FIG. 16, for example, or press-fit into engagement with the prepared acetabulum. The virtual model of the acetabulum can be used to design the location, orientation and amount or volume of bone that needs to be resected to receive acetabular cup 20 having corresponding protrusions 30A-E, for example. Determining the correct location and orientation of the polar axis or inclination angle of acetabular cup 20 is also important in the proper operative coupling of acetabular cup 20 into the prepared acetabulum.

Turning to the details of each protrusion, protrusion 30A is hereinafter described and is representative. As shown in FIG. 2, protrusion 30A includes a first end portion 34A, a central portion 31A, and a second end portion 36A, where central portion 31A separates the respective end portions. Protrusion 30A has a perimeter 32A such that its overall length is linear, although each end of protrusion 30A is rounded at an interface between protrusion 30A and outer surface 22. Central portion 31A has a partially cylindrical cross-sectional shape that extends linearly between end portions 34A, 36A. Each end portion is rounded between an end of central portion 31A and perimeter 32A abutting outer surface 22 such that a surface of each end portion 34A, 36A, is convex and curved in all directions. The shape of the protrusions is advantageous in that a bur tool is well suited to cut a groove in a bone that is sized to allow disposal of the protrusion therein.

As shown in FIG. 2, a length of each protrusion 30A-E is oriented at an angle of about twenty degrees relative to a plane through upper rim surface 26. Stated another way, the angle is about seventy degrees relative to a central axis of cup 20 through the pole. In some arrangements, the angle may be in a range from fifteen to twenty-five degrees. In other arrangements, the angle may be outside of this range to accommodate a desired application. The inclusion of protrusions on the outer surface of the cup increases its surface area and also provides the outer surface of the cup with a non-spherical shape. These characteristics increase the capacity of the cup to be fixed to a bone surface and the resistance of the cup to multi-axial forces that act against the cup when in an implanted state. Moreover, protrusions 30A-E are shaped to maintain implant stability and prevent loosening. It should be appreciated that in some embodiments, the protrusions are formed monolithically with the cup body and therefore the cup including the protrusions are integrally formed. However, it is also contemplated that these parts may be separately assembled.

Figure 4:
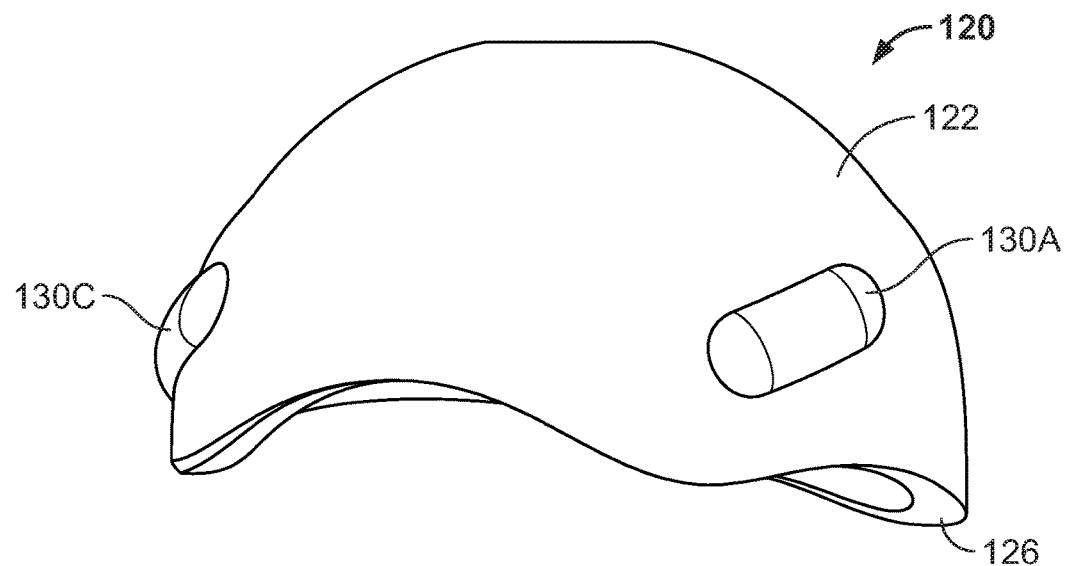
FIG. 4 is a side view of an acetabular cup according to one embodiment of the disclosure.
Figure 5:
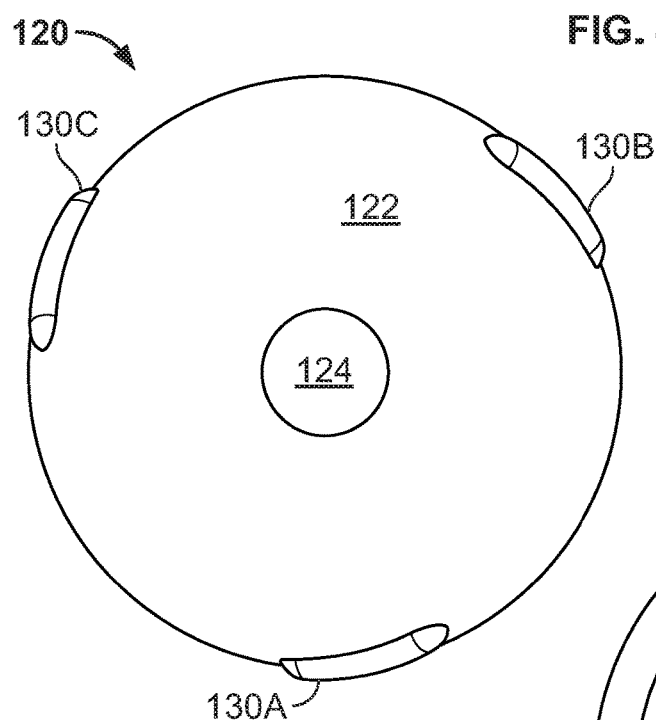
FIGS. 5-6 are bottom and top views of the acetabular cup shown in FIG. 4.
Figure 6:
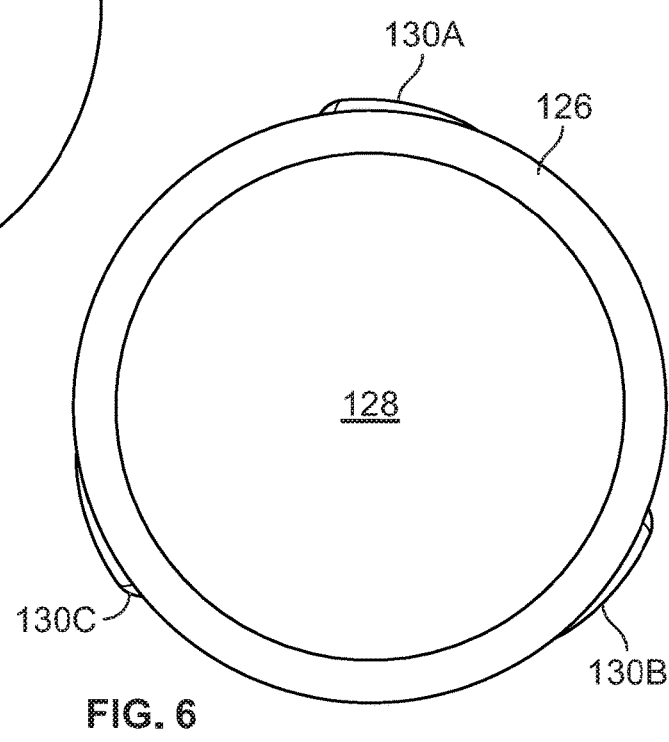

In one embodiment, the acetabular cup is an ADM acetabular cup 120 as shown in FIGS. 4-6. Unless otherwise stated, like reference numerals refer to like elements of above-described acetabular cup 20, but within the 100-series of numbers. And, unless otherwise noted, the variations and advantages inherent to acetabular cup 20 are also applicable to acetabular cup 120. Acetabular cup 120 includes an outer surface 122 that extends from a flat surface 124 surrounding a pole of the cup to an upper rim surface 126 that encloses an interior volume of the cup defined by a polished inner surface 128. Outer surface 122 is at least partially porous for bone ingrowth but in variations may have minimal porosity. Upper rim surface 126 has contours such that it is curved in a plane perpendicular to a central axis of cup 120 and is also curved relative to that plane, as best shown in FIG. 4. This curved shape provides improved alignment between a surface of the pelvic bone immediately outside the acetabular cavity and the rim. In particular, the curved shape of cup 120 aligns with the surface of the pelvic bone after the bone has been resected and otherwise prepared for implant placement. Additionally, one advantage of the shape of cup 120 is that a THA femoral component disposed in the cup has a greater range of motion relative to the range of motion possible with a standard acetabular cup design that includes a planar rim. Outer surface 122 includes three protrusions 130A-C disposed thereon. Each protrusion 130A-C is similarly shaped as protrusions 30A-E and is oriented at a similar angle. As shown in FIG. 5, protrusions 130A-C are equally spaced around a perimeter of the cup and are located at the same distance from flat surface 124.

Figure 7A:
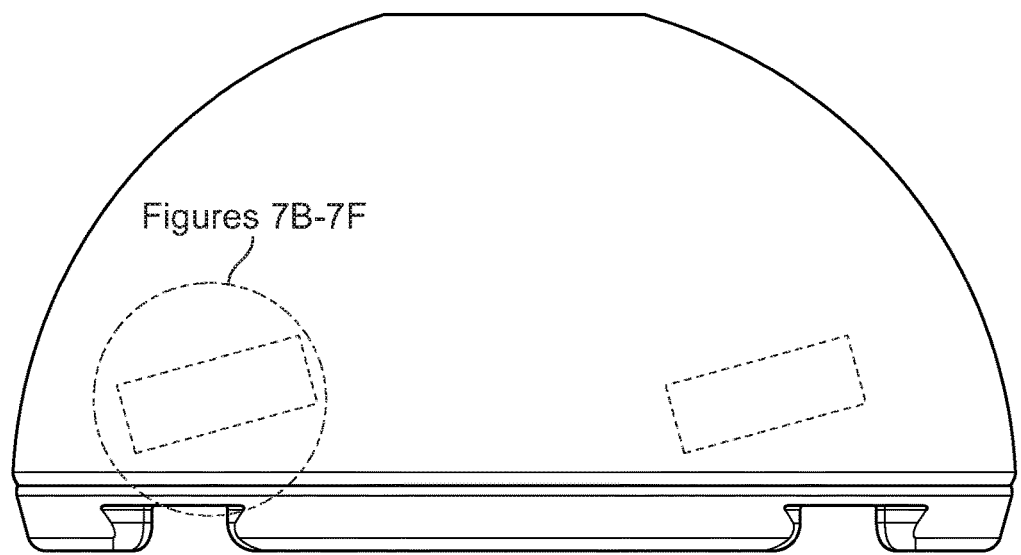
FIGS. 7A-7F are side views of protrusions according to distinct embodiments of the disclosure.
Figure 7B:
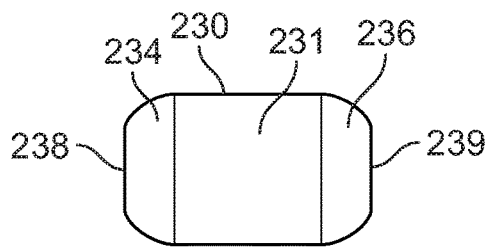

In other embodiments, the protrusion of the acetabular cup may vary from protrusions 30A-E and 130A-C. Some of these examples are shown in FIGS. 7B through 7F. Unless otherwise stated, like reference numerals refer to like elements of above-described protrusions 30A-E, but within the 200 through 600-series of numbers. In one example, protrusion 230 is shown in FIG. 7B. For this and other examples, protrusion 230 may be located on an outer surface of an acetabular cup as shown in FIG. 7A or in any other manner as contemplated by the disclosure. Moreover, multiple protrusions 230 may be included in a single acetabular cup. Protrusion 230 includes end portions 234, 236 that are separated by central portion 231. A longitudinal dimension through a combined shape of protrusion 230 is linear. Turning to the sub-portions, central portion 231 is linear with a convex, partially cylindrical surface that is generally uniform along its length. Each end portion 234, 236 has a convex surface that tapers to an end surface 238, 239, respectively. End surfaces 238, 239 are flat and perpendicular to the length of protrusion 230.

Figure 7C:
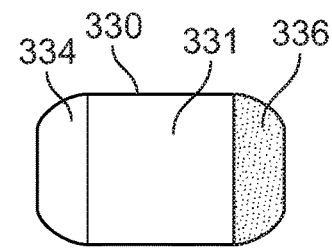

In another example, shown in FIG. 7C, a protrusion 330 includes end portions 334, 336 that are separated by central portion 331. End portion 336 is a leading edge that is polished to a greater extent than the remaining portions of the protrusion. The polishing of end portion 336 renders an acetabular cup onto which it is formed easier to insert into an acetabulum and also prevents the cup from backing out of a secured position. It should be appreciated that polishing of one or more protrusions is contemplated for incorporation into any one or more protrusions of the acetabular cups of the various embodiments described in the disclosure.

Figure 7D:
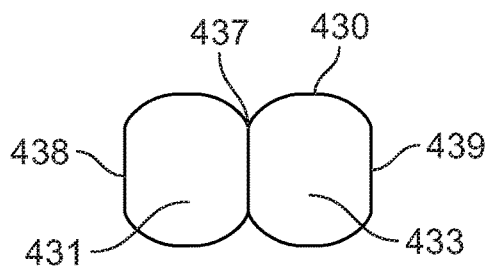

In yet another example, shown in FIG. 7D, a protrusion 430 includes two rounded portions 431, 433 that abut one another and each define a partially spherical shape. The portions abut in a manner such that a narrow slit 437 is formed therebetween. A low point of slit 437 remains above an outer surface of the acetabular cup. Each portion is a partial hemisphere, as shown, although terminal ends 438, 439 of protrusion 430 are defined by flat faces perpendicular to a length of the protrusion. Each portion 431, 433 is aligned so that a linear path extends through centers of each portion.

Figure 7E:
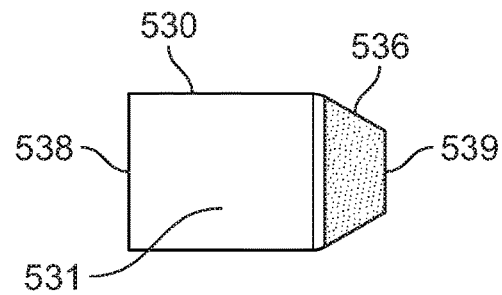

In another example shown in FIG. 7E, protrusion 530 includes a central portion 531 and a leading end portion 536. Leading end portion 536 is polished and is generally a partial conical shape that tapers toward a leading end surface 539. Central portion 531 has a partial cylindrical surface that extends from the leading end portion 536 to a rear end face 538 parallel to leading end face 539 and perpendicular to a length of protrusion 530.

Figure 7F:
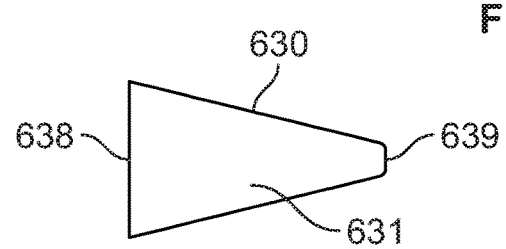

In yet another example shown in FIG. 7F, protrusion 630 includes a body 631 that is tapered throughout from a rear end surface 638 to a leading end surface 639, a size of the body becoming smaller toward the leading end. A surface of body 631 is rounded so that protrusion 630 is a partial cone shape.

The rotatably insertable acetabular cup, such as acetabular cup 20, 120, may be varied in many ways. For example, the cup may have any number of protrusions. In other examples, the protrusions may be spaced equally around a perimeter of the cup or they may be irregularly spaced. Similarly, the protrusions may be at different distances from a pole of the cup. In other examples, a length of the protrusions may be greater or less than that shown in the figures relative to a size of the cup. The protrusions may also have other shapes not shown. For example, a protrusion could be any shape with a tapered leading end. Different protrusions on the same cup may also have different lengths and/or shapes. An angle of the protrusions relative to an axis through the pole of the cup may be different for separate protrusions on the same cup.

Figure 8:
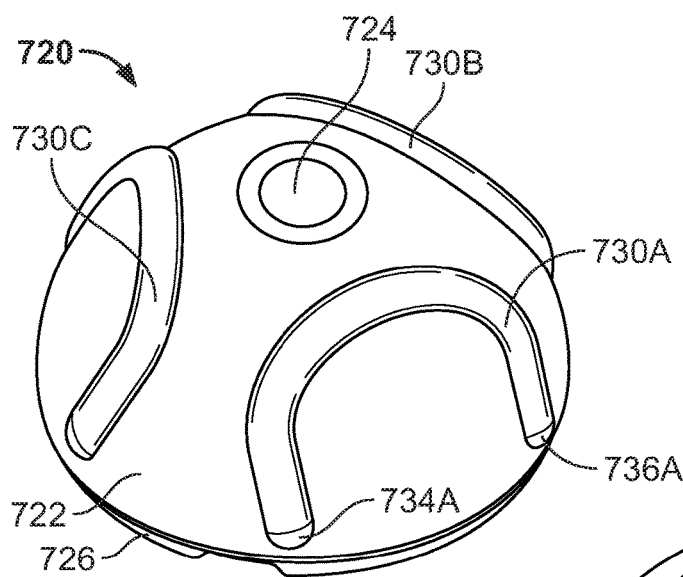
FIG. 8 is a perspective view of an acetabular cup according to one embodiment of the disclosure.

In further embodiments, an acetabular cup may have other patterns of protruding surfaces, such as those shown in FIGS. 8 through 13. Unless otherwise stated, like reference numerals refer to like elements of above-described acetabular cup 20, but within the 700 through 1200-series of numbers. Each of the acetabular cups illustrated in FIGS. 8-13 have surface geometry shaped to lock the cup in six degrees of freedom. FIG. 8 illustrates an acetabular cup 720 with three separate protrusions 730A, 730B and 730C, extending from outer surface 722. Each protrusion is U-shaped with ends of the U adjacent to the upper rim 726. For example, protrusion 730A extends between ends 734A, 736A. Accordingly, a bottom of the U is closest to opening 724 in a polar region of cup 720. Acetabular cup 720 is symmetrical about at least one axis.

Figure 9:
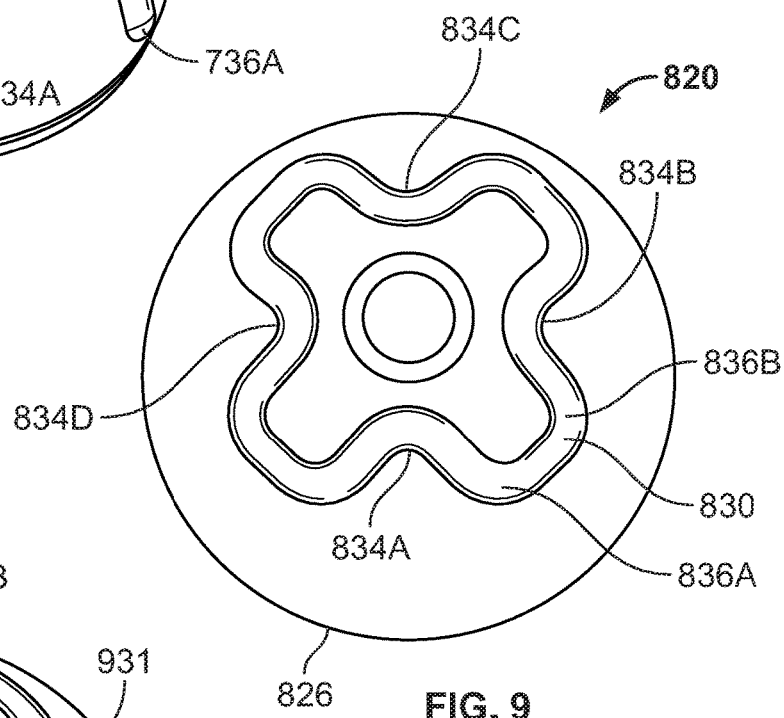
FIG. 9 is a perspective view of an acetabular cup according to one embodiment of the disclosure.

FIG. 9 illustrates an acetabular cup 820 according to yet another embodiment of the disclosure with a protrusion 830 forming an enclosed perimeter on outer surface 822. Protrusion 830 includes a plurality of bends such that separate segments of protrusion 830 are at different distances, or at a varying distance, from opening 824 at a pole of the cup. Protrusion 830 forms a shape similar to a plus symbol and includes four segments approximately equidistant from one another and parallel to upper rim 826, including a segment from reference numeral 836A to 836B. At the end of each of these segments the protrusion extends inward to corners closest to the pole including corners 834A-D. Acetabular cup 820 is symmetrical about two perpendicular axes from multiple reference axes.

Figure 10:
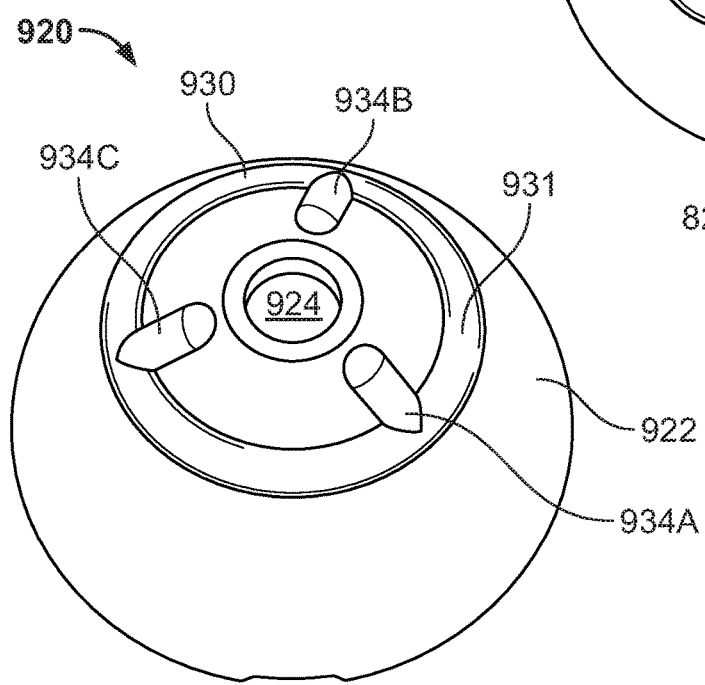
FIG. 10 is a perspective view of an acetabular cup according to one embodiment of the disclosure.

FIG. 10 illustrates an acetabular cup 920 according to another embodiment of the disclosure. Acetabular cup 920 includes a protrusion 930 with a circular portion 931 extending circumferentially around an opening 924 over a pole of the cup at a single radius. Protrusion 930 also includes extensions 934A-C that extend toward the pole of the cup from circular portion 931. Each extension 934A-C has an end remote from circular portion 931 that is spaced apart from opening 924. Each extension 934A-C is spaced equally around the pole of the cup. Acetabular cup 920 is symmetrical about at least one axis.

Figure 11:
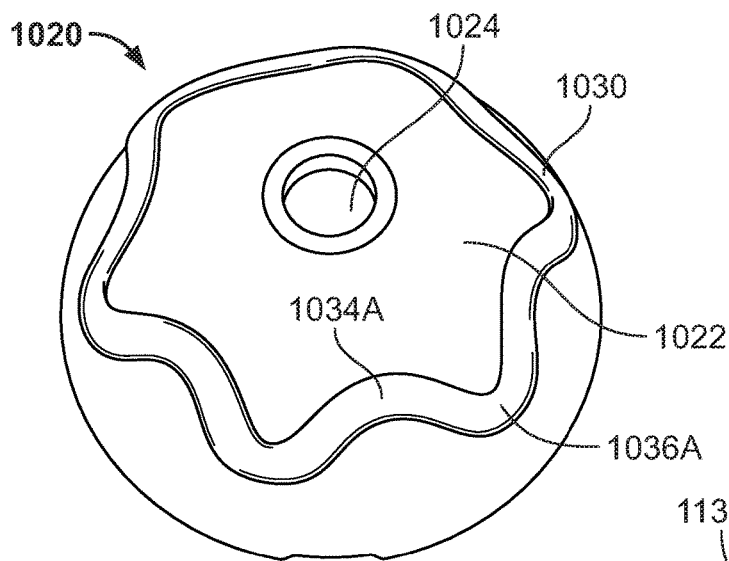
FIG. 11 is a perspective view of an acetabular cup according to one embodiment of the disclosure.

FIG. 11 illustrates an acetabular cup 1020 according to one embodiment of the disclosure. Acetabular cup 1020 includes a protrusion 1030 that defines an enclosed perimeter on an outer surface 1022. Protrusion 1030 has a wave pattern with curved bends that oscillate between near-polar and near-equatorial limits, such as near-polar bend 1034A and near-equatorial bend 1036A. Acetabular cup 1020 is symmetrical about two perpendicular axes from multiple reference axes. The near-polar and near-equatorial limit is a single limit reached by all bends on the protrusion, though in variations the limit may vary at different locations around the perimeter of the protrusion.

Figure 12:
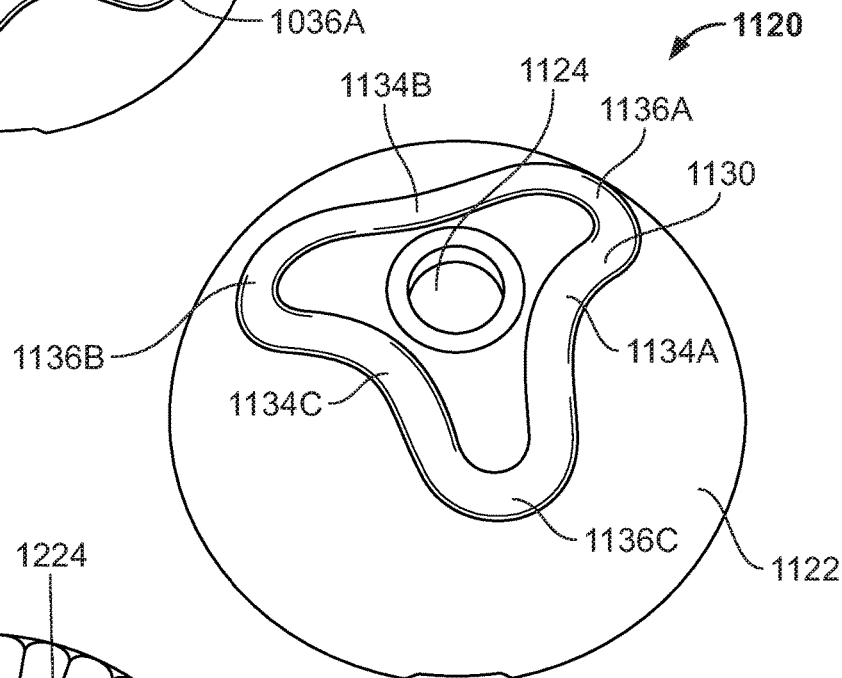
FIG. 12 is a perspective view of an acetabular cup according to one embodiment of the disclosure.

FIG. 12 illustrates an acetabular cup 1120 according to one embodiment of the disclosure. Acetabular cup 1120 includes a protrusion 1130 that defines a closed perimeter on outer surface 1122. Protrusion 1130 includes three bends 1134A-C closest to the pole of the cup extending through opening 1124 and three bends 1136A-C furthest from the pole, each bend being rounded so that the protrusion has an alternating concave and convex edge over its perimeter. Acetabular cup 1120 is symmetrical about at least one axis.

Figure 13:
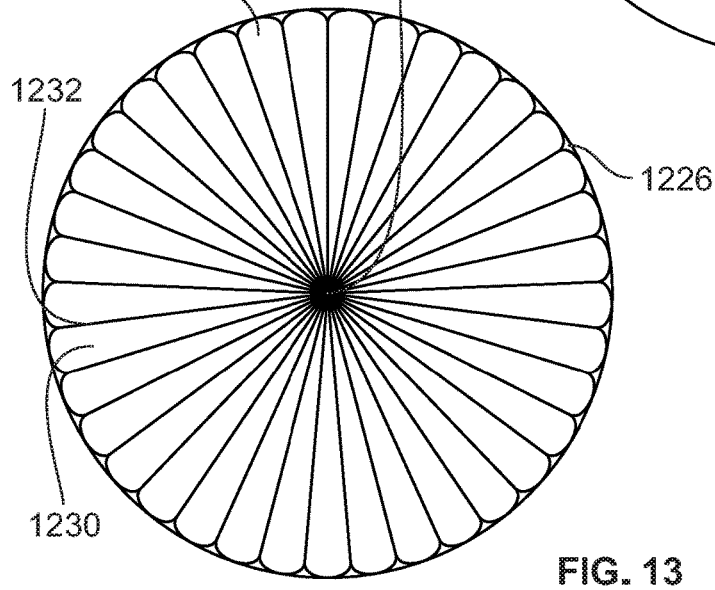
FIG. 13 is a bottom view of an acetabular cup according to one embodiment of the disclosure.

FIG. 13 illustrates an acetabular cup 1220 according to one embodiment of the disclosure. FIG. 13 is a bottom view that shows a pole 1224 of the cup to an edge of an upper rim 1226. Acetabular cup 1220 includes a plurality of radially extending protrusions 1230 on an outer surface 1222, each extending from pole 1224 to upper rim 1226. Protrusions 1230 abut one another around a perimeter of acetabular cup 1220 such that troughs 1232 are formed in between each protrusion 1230. Protrusions 1230 cover an entirety of outer surface 1222, although in variants, it is contemplated that spacing may be included between the protrusions. In other variations, it is contemplated that the protrusions may be wider so that there are fewer in total on the outer surface. In further variations, the protrusions themselves may vary in size within a single acetabular cup. Acetabular cup 1220 is advantageous in that it provides improved resistance against axial rotation.

The features on an outer surface of an acetabular cup such as those illustrated in FIGS. 8-13 may be varied in many ways. For example, the location of the protrusion may be closer to or further from the pole than shown in the figures. The shape may also be modified to suit a desired application. For example, The "U" shaped bends of FIG. 8 may have ends that extend inward toward each other. Other variations of this nature are also contemplated. Additionally, a height of the protrusion on an acetabular cup may vary over its length. A single acetabular cup may have any number of protrusions. These protrusions may all be the same or there may be two or more types on a single cup. A location of the protrusions may be further or closer to a pole of the cup than in the illustrated embodiments. The patterns of the protrusion may be modified to have a greater number or fewer number of bends or to vary in distance from the pole around a perimeter of the protrusion. Additionally, the geometric features on the outer surface of the cup may be reversed so that instead of protrusions, the outer surface has grooves recessed therein. In such examples, an acetabular bone surface is cut to form protrusions that are received within the grooves of the implant.

In another aspect, the acetabular cup contemplated herein may be included as part of a kit. In one embodiment, a kit includes two acetabular cups, where each cup has a unique size. In another embodiment, a kit includes two acetabular cups, where each acetabular cup has a unique shape. In another embodiment, a kit includes a group of acetabular cups that are all the same. In yet another embodiment, a kit includes a first set of acetabular cups that are all the same along with a second set of acetabular cups different from the first set. It should be appreciated that the above embodiments are illustrative and that any combination of the above embodiments may be used to form a kit.

In some embodiments, a kit includes an acetabular cup and one or more additional hip implant components. For example, a kit may include an acetabular cup and one or more of a liner, femoral head, femoral implant (stem), and other hip related components. Any number and variety of hip implant components may be included with an acetabular cup in a kit, and any combination of acetabular cups such as those described in the embodiments above may be included in a kit with one or more sets including the remaining components needed to provide a complete hip implant. In other embodiments, accessories for an acetabular cup such as implantation or removal tools, or additional components that are implanted along with the acetabular cup may also be included.

The kit may be varied in many ways. For example, the various combinations of elements of any contemplated kit may be included in a single package or distributed among multiple packages. In other examples, the kit contemplated herein may be accompanied by an instruction manual on how to perform one or more of the methods of using the contents of the kit.

In another aspect, the present disclosure relates to manufacture of an acetabular cup through the use of additive layer manufacturing methods, e.g., three-dimensional printing. Examples of additive layer manufacturing (ALM) techniques that may be used include electron beam melting, selective laser sintering (SLS), selective laser melting (SLM), and other three-dimensional (3-D) processes. When employing these technologies, articles are produced in layerwise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the acetabular cup. After the sintering or melting of the powder on one particular layer, an additional layer of powder is dispensed, and the process repeated, with sintering or melting taking place between the current layer and the previously laid layers until the acetabular cup is complete. In one example, a high energy beam is emitted from a beam-generating apparatus to heat metal powder sufficiently to sinter and preferably to at least partially melt or fully melt the metal powder. High energy beam equipment for manufacturing such structures may be one of many commercially available. The beam generation equipment may also be a custom-produced laboratory device. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664, the disclosure of which is incorporated by reference herein. The SLM and SLS technologies enable direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics.

Other non-powder based additive manufacturing technologies are also known to produce high resolution and dimensionally accurate articles. For example, in fused filament fabrication (FFF) or Plastic Jet Printing (PJP), strands of molten material are extruded from a nozzle to form layers onto a substrate in which the material hardens upon extrusion. Using digital light processing (DLP), photosensitive resin plastic is cured by light and built layer by layer from the bottom-up or a vat of liquid polymer is exposed to balanced levels of ultraviolet light and oxygen to produce a part often from the top-down. In inkjet 3D printing, a liquid binding material is selectively deposited across a thin layer of a powder and the process is repeated in which each new layer is adhered to the previous layer.

In some embodiments, an existing acetabular cup, such as an existing hemispherical cup, may be modified through three dimensional printing to add protrusions onto its outer surface. Put another way, three dimensional printing may be used to add surface features onto the outer surface of the acetabular cup to alter the existing geometry.

In another aspect, the present disclosure relates to a method of implanting an acetabular cup into an acetabulum. In one embodiment, the method is performed semi-autonomously with the assistance of a robotic manipulator for the implantation of a THA cup. Throughout the disclosure, the term "robotic manipulator" is used interchangeably with "robot." The robot forms part of a larger system (not shown) that includes a computer, memory, controller, inputs and outputs, and a navigation system, which are interconnected with one another. The inputs include a keyboard or other user interface and the output includes at least a display that outputs images and/or data associated with the three dimensional model and the surgical plan, among other information pertinent to the surgery. One function of the robot is to store data that relates to the location of various elements involved in the performance of the method. These include data for the location of the implant, the surface features on the implant, the cutting tool and the planned bone cuts. The robot is configured to operate with haptic guidance, is set up for connection to a cutting tool, such as a bur, and is set up for connection to a rotatable driver for seating of the acetabular cup. Through the combination of the programmable robot and haptics, the system is configured to provide force feedback and visual guidance during surgery, as described in greater detail below.

Figure 26:
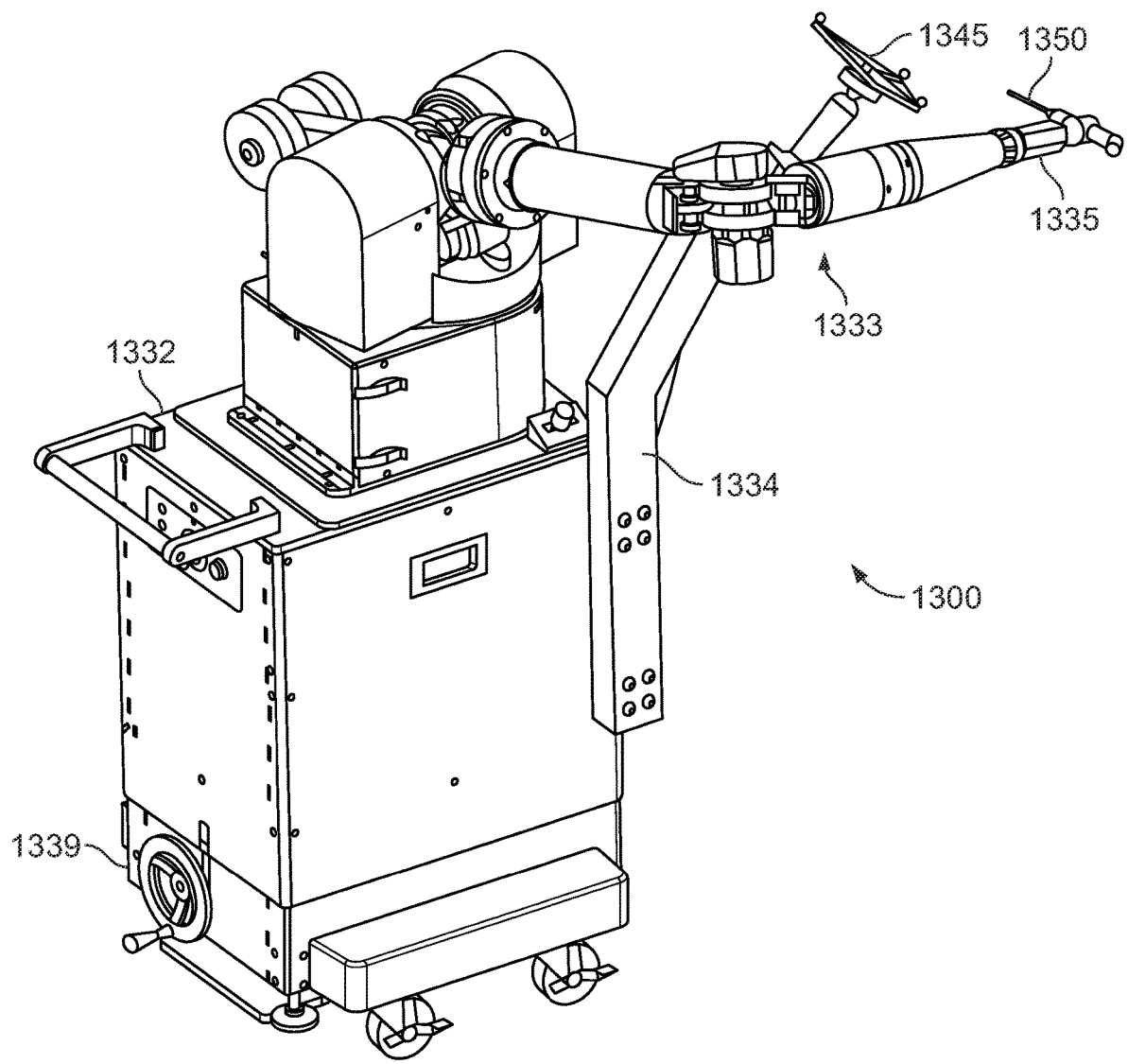
FIG. 26 illustrates a robot used to perform a method of implanting an acetabular cup according to one embodiment of the disclosure.

The robot with haptics may be as described in U.S. Pat. App. Pub. No. 2006/0142657 (the '657 Publication), hereby incorporated by reference herein in its entirety. The robot of the '657 Publication is shown in FIG. 26 as robot 1300 and includes a base 1332, platform 1339 and arms 1333, 1334 that extend from base 1332. Arm 1334 extends to a haptic device tracker 1345 while arm 1333 includes a plurality of linkages and extends to an end effector 1335 that connects to a tool 1350, such as a bur. Another example of a robot is described in U.S. Pat. No. 7,831,292, hereby incorporated by reference herein in its entirety. In alternative approaches described in greater detail below, the method may be fully automatic or may include certain steps performed manually by a user. The term "user" refers to an individual that performs the surgical method. This may include an operator of the robot or a surgeon, for example.

Although the initial preparation and planning steps of the method are not illustrated, the remaining steps of the described method are illustrated in FIGS. 14-18. Initially, the anatomy around the hip is scanned to collect data about the patient. In some examples, the scans may generate images for processing. More than one scan and/or more than one type of scan may be performed as deemed appropriate under the surgical circumstances. It should also be appreciated that additional scans may be performed during later stages of the procedure. A physical scope of the scan may vary as a function of the circumstances. The scans are stored in the memory of the computer and processed to develop a three dimensional model of the relevant anatomy for the patient receiving the implant. With a baseline model generated, the area in and around the target pelvic bone is registered to associate the data in the model with the real time actual locations of the relevant anatomy on the patient. With registration complete, a user may view the model on the display while it is linked to the actual location of the target hip features as they lie during the procedure. Detailed examples of the above method steps are provided in U.S. Pat. App. Pub. No. 2017/0181755 and U.S. Pat. No. 8,617,171, the disclosures of which are incorporated by reference herein in their entirety. It should be appreciated that the details of the steps up to the registration of the anatomy of the patient may vary and the order of such steps as described is not limiting.

In some variations, the system used for the method may employ a robot that includes both a cutting instrument and imaging hardware. Such a robot is advantageous in that it streamlines workflow and reduces the need to move around the various parts of the system during the procedure and/or reduces the need for repeated registrations of one or more elements of the system. One example of such a robot is described in U.S. Pat. App. Pub. No. 2014/0188132, hereby incorporated by reference herein in its entirety.

With the anatomy registered, surgical planning, also referred to herein as planning, for the surgery surrounding pelvic bone 10 is performed. In short, planning involves establishment of the particular bone structure, including location, size and shape, to be cut with the robot. Because the acetabular cup is already manufactured at this stage and thus has predetermined surface features including protrusions for rotational engagement with bone, the dimensions of the cup are used as a guide to determine how the acetabulum will be cut. In particular, angled protrusions 30A-E of acetabular cup 20 will need to align with the grooves (shown as reference numerals 14A-E when cut) formed within the acetabulum so that the cup may be rotated into a fixed position within the acetabular cavity. In this manner, the bone cuts will be positioned equally with the surface geometry of the acetabular cup.

Turning to the details of the required bone cuts, a first cut will be based on the amount of bone removal needed to create a generally hemispherical socket sized to closely match an outer surface of the acetabular cup, i.e., concave surface 12. Then, a series of second cuts will be recessed relative to the first cut and will be in the form of longitudinally extending grooves partially offset from one another along a perimeter 15 of acetabular surface 12. A width of these grooves will be sized to closely match a width of the protrusions, and a length and alignment of each groove will be established so that the acetabular cup is rotatable within the grooves to a sufficient extent to fully seat the cup within the acetabular cavity. To render the surgical plan executable, data for the bone cuts is saved into the memory linked to the computer and incorporated into the three dimensional model described above. With the precise identification of anatomical locations already in the model, this approach allows for very precise cutting of the bone so that when the cup is inserted into the acetabular cavity, the bone surface and the acetabular cup will predictably fit closely with one another. In some variations of the method, the computer is used to generate boundary volumes for disposal of the implant into the resected bone as part of the planning process. In particular, the model may generate a range of acceptable cut volumes and/or cut paths in the bone that will allow for a satisfactory seating of the implant. Some examples describing the details of these planning steps are provided in U.S. Pat. App. Pub. No. 2017/0000562, hereby incorporated by reference herein in its entirety.

It should be appreciated that the exact dimensions of the planned cut may be varied based on results of an optional bone density review that may warrant deeper or shallower cuts. Some examples of how bone density of a particular patient may be used to optimize implant geometry are described in U.S. Pat. App. Pub. No. 2015/0119987, hereby incorporated by reference herein in its entirety. Similarly, the depth of the cuts may be slightly shallower to increase friction between the protrusions and the bone or deeper to reduce friction.

Turning to the operation of the robot and the bur, the robot, such as robot 1300, is connected to the controller and/or computer, along with the navigation system, to ensure data from the robot including the bur location is overlaid with the three dimensional model. The bur is then connected to the robot if not already connected. It should be appreciated that although the method is described with the use of a bur as a cutting tool, it is contemplated that other cutting tools may also be used. Through the connection of the robot to the overall system, advancement of the bur into the pelvic bone 10 will be visible on the display showing the three dimensional model. As shown in FIG. 14, bur tool 40, e.g., a ball bur tool, is then advanced to pelvic bone 10 while the navigation system tracks the coordinates of the bur and relays such information to the computer to show a location of bur 40 on the display that shows the three dimensional model. During this step, the model is viewable via the display and the surgical site is also viewable via direct visualization.

The user references the cut plan on the model to guide bur 40 to acetabular surface 12 to make the first cut, which is the initial surface cut that corresponds to the size and shape of the generally hemispherical outer surface 22 of acetabular cup 20. As the user performs the cut, the location of the bur tip is fed back to the computer and associated with the three-dimensional model information. The model has a predetermined cut depth based on the surgical plan programmed as noted above. As bur 40 reaches the bounds of such depth or the outer limits of the cut near a perimeter 15 of the acetabular cavity, the haptics of the robot generate increasing feedback, such as vibration, resistance, or a combination of the two, among others, to prevent the user from cutting outside of the predetermined limits of the planned cut volume. In this manner, the bone cut is precise and does not deviate from the surgical plan. Further detail regarding how haptics may be used to control cutting limits and volume are described in U.S. Pat. App. Pub. No. 2015/0080717, hereby incorporated by reference herein in its entirety. When this step is complete, acetabular surface 12 is sized and shaped to closely fit a size and shape of the convex rounded outer surface 22 of the acetabular cup therein. Put another way, the cut acetabular surface is the inverse of the outer surface of the cup. However, the second series of cuts to create grooves in the acetabular surface must still be performed prior to insertion of the cup into the cavity.

Similarly to the cut of the concave surface 12 of the acetabulum that defines the cavity, bur tool 40 is used to cut predetermined grooves in surface 12 in accordance with the three dimensional model parameters as established during the planning stage of the procedure described above. The application of bur tool 40 to the acetabular surface to cut the grooves is shown in FIG. 14. Again, as with the initial cut of the acetabular surface, the user will direct the bur tool along the surface of the acetabulum within a predetermined cut path for the tool to create each groove 14A-E separately within the surface. The predetermined limits of the cut, including width, depth and cross-sectional shape, are programmed in the three dimensional model and are associated with coordinates that are continuously compared with coordinates of the bur tool. In this manner, when the bur tool reaches the limits of the predetermined cut path during use, the haptics of the robot provide increasing feedback in the same manner as occurs during execution of the first cut. Again, as with the first cut, the robot-assisted bur tool forms each groove with exacting tolerances as established through the three dimensional model so that the formed grooves 14A-E are sized and positioned to receive respective protrusions 30A-E on acetabular cup 20. The grooves are the inverse shape of the protrusions, so an exact or close to exact fit between the two in accordance with the surgical plan is expected each time the procedure is performed. Further, with the correlation of the respective geometries, cup 20 is rotatable to fully insert and fix the cup in the acetabular cavity.

As is apparent by the description, one advantage of the described method is that all of the required bone cutting may be performed with a bur tool, and that reamer baskets are not required to complete the requisite cutting. Another advantage is that the depth of cut into the acetabulum and the shape and location of the grooves in the acetabulum may be customized for the size of a particular bone within a patient. With design tolerances set forth in the surgical plan executed accurately with robot guided cutting, there is no need to undercut the acetabular cavity and then impact the acetabular cup to achieve fixation. Other related advantages include the elimination of impact forces applied to the patient and the elimination of potential injury to the user that could otherwise be incurred through the application of impaction forces during the procedure. Yet another advantage is the reduced number of surgical components required to complete the procedure. A single size bur is used in place of a series of reamer baskets that vary in size.

FIG. 14 illustrates that formed grooves 14A-E are staggered around a perimeter of acetabulum 12 and each have a length extending from a first end close to a perimeter 15 of acetabulum 12 at an upper end to a second end closer to a lower end of acetabulum. See first end 14E-1 and second end 14E-2 for groove 14E, for example. A second end of each groove is positioned directly below a first end of an adjacent groove, although in variants adjacent grooves may not overlap in this manner. The variation in depth of each groove from the first end to the second end renders the path of the groove curved in two directions, relative to a plane through perimeter 15 of the cup and relative to a plane perpendicular to the plane through the perimeter.

Figure 15:
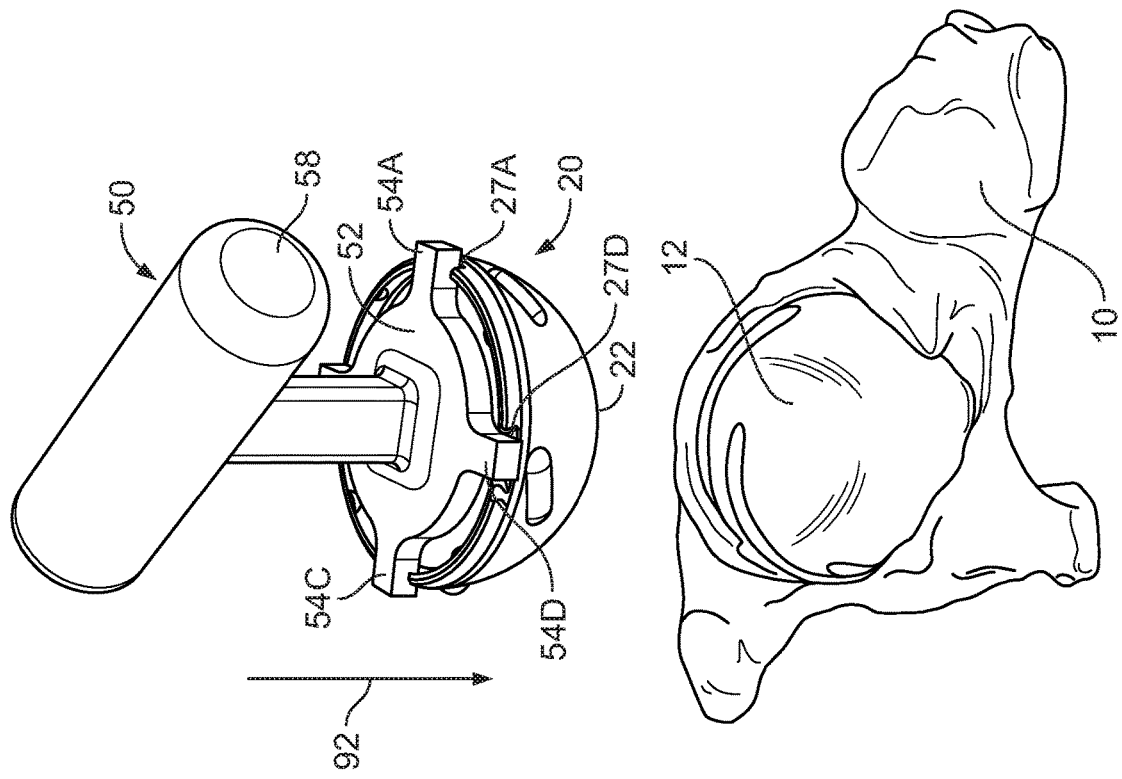

With the bone surface of acetabulum 12 prepared and grooves 14A-E cut, acetabular cup 20 is secured to a rotatable driver in the form of an insertion tool 50 as shown in FIG. 15 to prepare the cup for fixation to the acetabulum. Of course, cup 20 may be secured to insertion tool 50 at any time prior to this step. As shown in FIG. 15, insertion tool 50 includes a handle 58 with a base 52 having engagement arms 54A-D that extend therefrom. In a variant, the method may be performed with a different insertion tool. Each engagement arm 54A-D includes a tab-type end structure that is engaged within corresponding recesses 27A-D in upper rim 26 of the cup. Through the inclusion of engagement arms 54A-D, tool 50 is uniformly engageable with cup 20. The securement between the tool and the cup allows a non-limiting and uniform application of torque to be applied to the cup through the tool as it is rotated into a fully seated position within the cavity. Once acetabular cup 20 is secured to insertion tool 50, the insertion tool is connected to the robot so that the cup may be seated into the acetabular cavity with haptic guidance. Additionally, the acetabular cup may include a marker, tracker or other indicator (not shown) so that the cup appears on the display as it is advanced into the pelvic bone. In one example, trackers and torque/force sensors are attached to the cup and handle to provide real time data for haptic response, including guidance and feedback. The haptics can provide feedback as the protrusions of the cup move through respective grooves in the acetabulum and as the cup advances to the bottom surface of the cavity.

The tool is advanced toward the acetabulum as indicated by reference numeral 92 in FIG. 15. Handle 58 of tool 50 is then manipulated to align protrusions 30A-E on outer surface 22 of acetabular cup 20 with respective grooves 14A-E on the acetabular surface, as shown in FIG. 16. If the protrusions are not aligned with the grooves when the cup abuts the cavity, the haptics may generate feedback to keep the user's direction of the insertion tool within the predetermined insertion path. Once aligned, handle 58 of tool 50 is rotated as indicated by reference numeral 94 to advance protrusions 30A-E into respective grooves 14E. The grooves are cut in a manner so that a lower end of each groove is at a first distance from a pole of the acetabulum and the leading end of each protrusion is at the first distance from a pole of the acetabular cup. The grooves have a length sufficient to ensure that the acetabular cup is in the fully inserted and fixed position before the protrusions reach the ends of the grooves. In alternative surgical plans, the grooves may be only marginally longer than the rotational path required to fully insert the cup. In still other alternatives, each groove may be a slightly different length. Once fully seated, outer surface 22 of acetabular cup 20 is flush with acetabular surface 12, as shown in FIG. 17. Thus, through this method, acetabular cup 20 is disposed exactly or nearly exactly within the acetabular cavity in a fixed manner without a need to form an undersized acetabular surface in preparation for cup placement. In the fixed position, the acetabular cup is locked in six degrees of freedom. Tool 50 is then removed from acetabular cup 20 leaving the cup fixed to the acetabulum as shown in FIG. 18.

One advantage of the above described method is that the acetabular cup can be fixed to the bone accurately and with more than sufficient resistance to back out without the need for the application of impaction forces during the procedure. Another advantage is that other implant components do not need to be changed in view of the methods described in the present disclosure. For example, a polymer liner for disposal within the acetabular cup may be the same as that used in previously known procedures without compromising the effectiveness of the methods herein. Thus, certain components may be interchangeable between systems. Moreover, steps for fixation of implant components other than the acetabular cup would remain unchanged with the methods described herein. It should be appreciated that the method shown in FIGS. 14-18 applies to implantation of acetabular cups having a planar upper rim, such as THA cups, which include acetabular cup 20.

In another embodiment, an ADM cup that has a variable depth upper rim, such as is shown in FIG. 4, is used as the cup for a hip replacement procedure. The cutting and implantation steps of this embodiment are illustrated in FIGS. 19-23. Unless otherwise stated, like reference numerals refer to like elements of above-described acetabular cup 20, but within the 100-series of numbers. And, unless otherwise noted, the preliminary steps of three dimensional model generation, registration and planning are the same as those described for the implantation of a THA cup described above and shown in FIGS. 14-18. Similarly, the steps for cutting bone in the acetabulum and for insertion of the cup are the same as those described for the THA cup.

Figure 21:
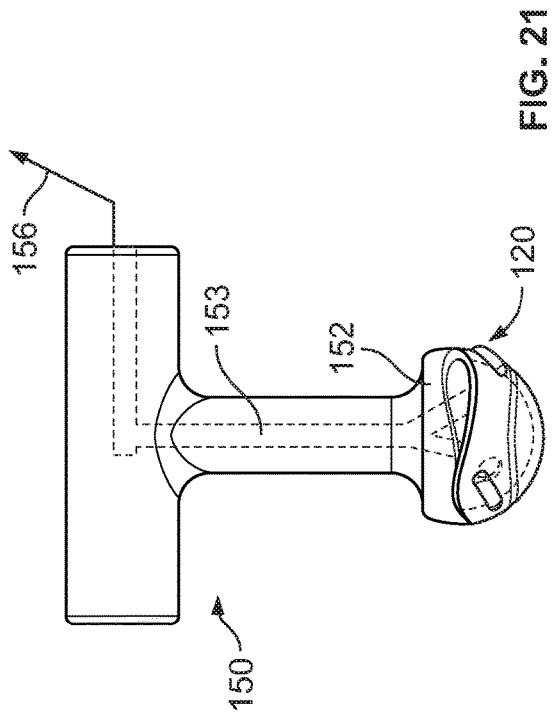
Figure 19:
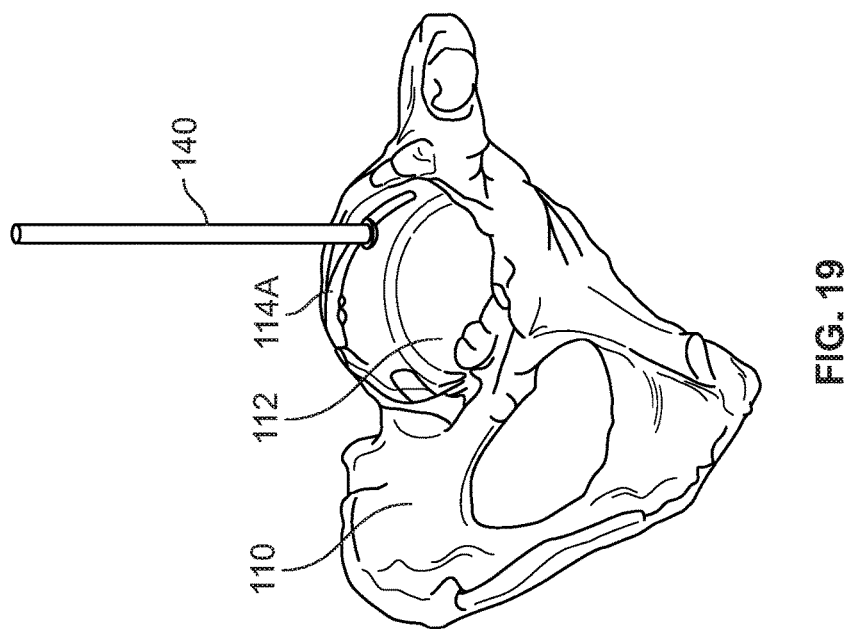

Initially, and as shown in FIG. 19, acetabular surface 112 and grooves such as groove 114A, are cut and prepared with a bur tool 140 semi-autonomously with the robot and haptic guidance. A T-handle insertion tool 150 is then engaged with acetabular cup 120 in preparation for insertion of acetabular cup 120 into the acetabulum within pelvis 110. T-handle insertion tool 150 is vacuum enabled and includes a base 152 with a porous engagement surface 154 having a hemispherical shape to match an inner surface of acetabular cup 120. The engagement surface may be made of rubber. Inside the body of T-handle tool 150 is a vacuum channel 153 extending from porous engagement surface 154 to an external vacuum source 156, as shown in FIG. 21. To hold acetabular cup 120 securely in place on surface 154 of tool 150, the vacuum is activated, and the suction drawn through engagement surface 154 brings a polished inner surface 128 of cup 120 flush onto the matching engagement surface, as indicated by reference numeral 191 and shown in steps from FIG. 20 to FIG. 21. The varying contours on upper rim 126 of cup 120 correspond to contours on a ledge 158 on tool 150 so that rim 126 follows ledge 158 around respective perimeters, as shown in FIG. 21. While the vacuum remains active, acetabular cup 120 remains engaged to T-handle tool 150.

Figure 23:
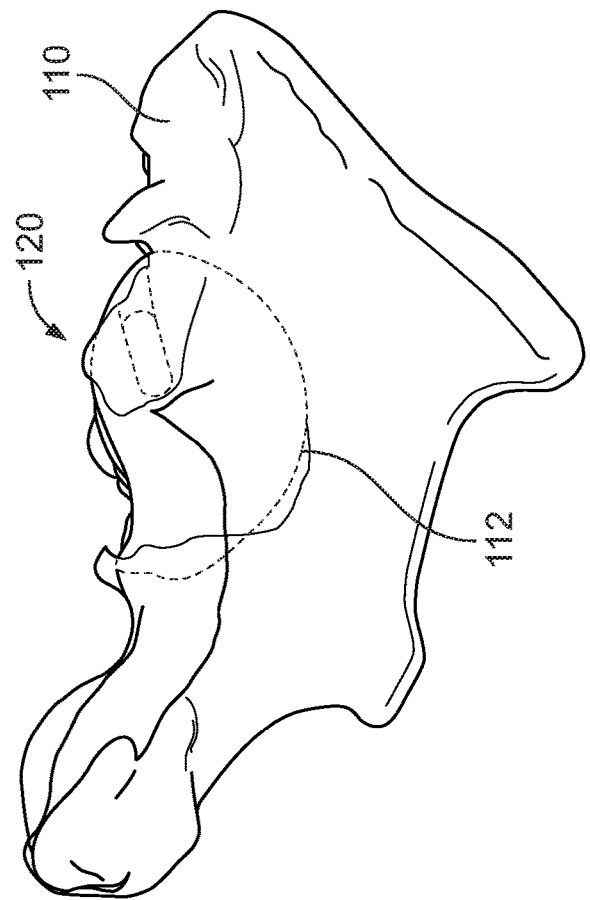
Figure 22:
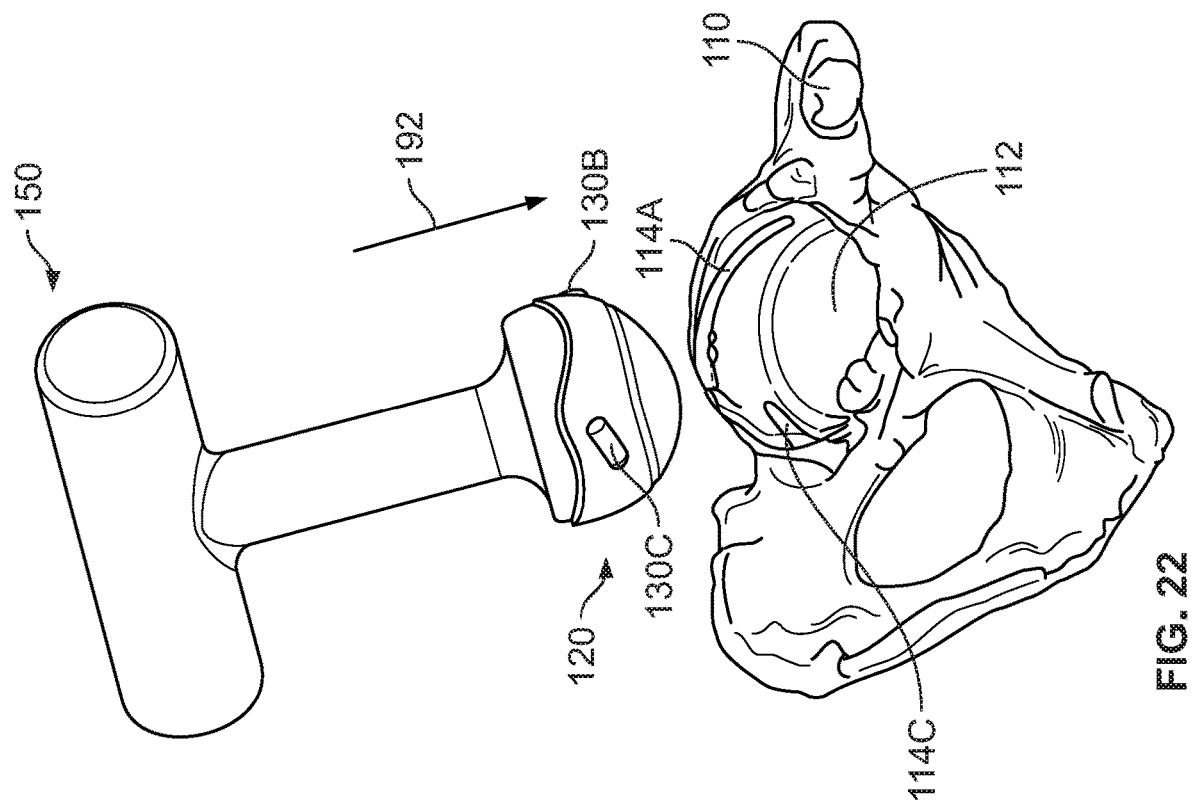

If not already connected, tool 150 is now connected to the robot so that it may be operated semi-autonomously. The combined tool 150 and acetabular cup 120 are brought to the prepared acetabulum, as indicated by reference numeral 192 and shown in FIG. 22. From this step, the acetabular cup is advanced into the bone. As described above, the haptic guidance associated with the robot provides feedback if the cup is engaged or rotated outside of a predetermined insertion path within the acetabular cavity. During insertion, protrusions 130A-C engage with and rotatably advance within and along a length of grooves 114A-C. In some examples, one or more of the protrusions do not reach the end of the grooves in the fully seated position and in others one or more of the protrusions may reach the end of the grooves. Once seating of the cup is complete, tool 150 is removed by further twisting of the handle. Alternatively, the direction of the vacuum may be reversed to remove the tool or the vacuum may simply be deactivated. FIG. 23 illustrates the fully seated position of the acetabular cup where outer surface 122 of acetabular cup 120 is flush with acetabular bone surface 112. One advantage of this approach is, again, the elimination of the need for impaction instruments or of the application of impaction forces in general. Another advantage is the reduction of the number of tools required to seat the cup, i.e., only a single T-handle insertion tool is used.

It should be appreciated that the methods described above are not limited to application with acetabular cup 20 and 120. For example, these methods can also be employed with acetabular cups having protrusions such as those shown in FIGS. 7B through 7F and other rotatably inserted acetabular cups contemplated herein. Additionally, when the acetabular cups shown in FIGS. 4-7 are fully seated, such cups are locked in six degrees of freedom with respect to the bone in a manner similar to the locking of acetabular cup 20 describe above.

Figure 24:
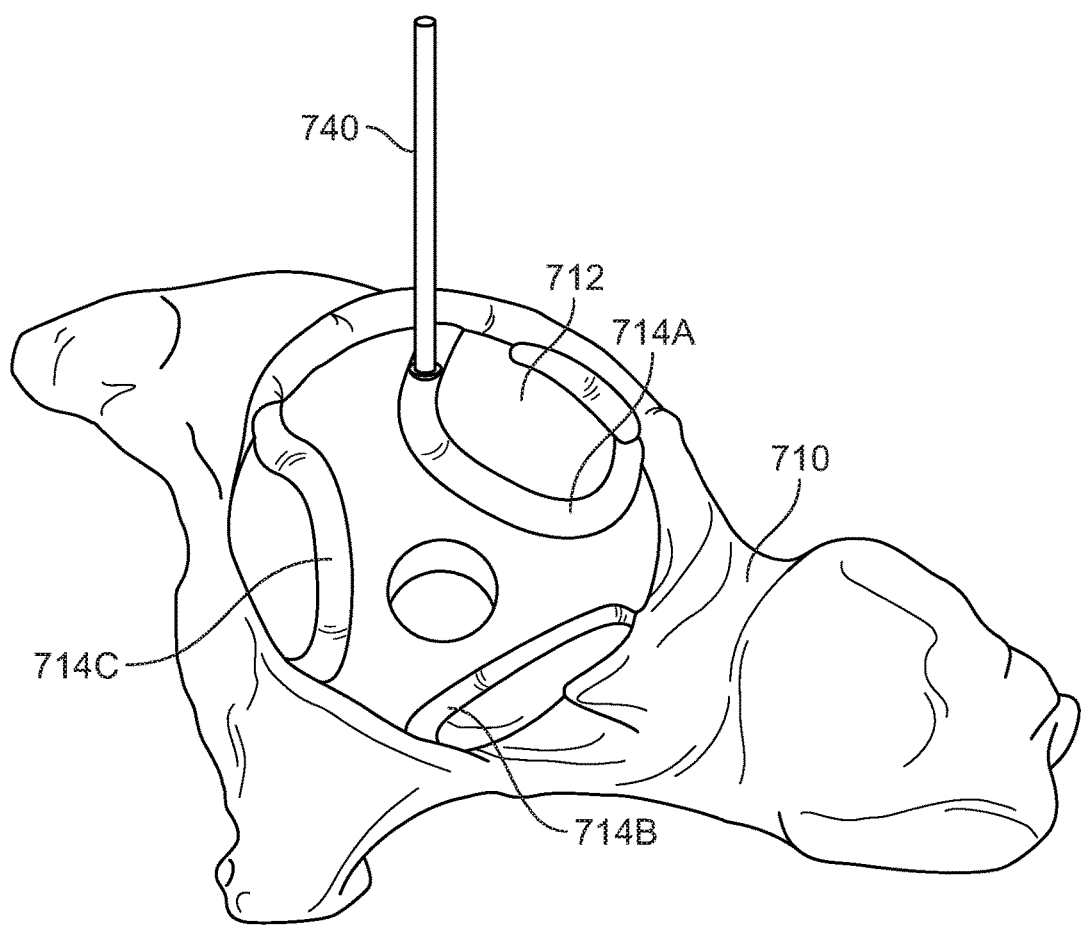
FIGS. 24-25 illustrate steps in a method of implanting an acetabular cup into an acetabulum of a patient according to one embodiment of the disclosure.
Figure 25:
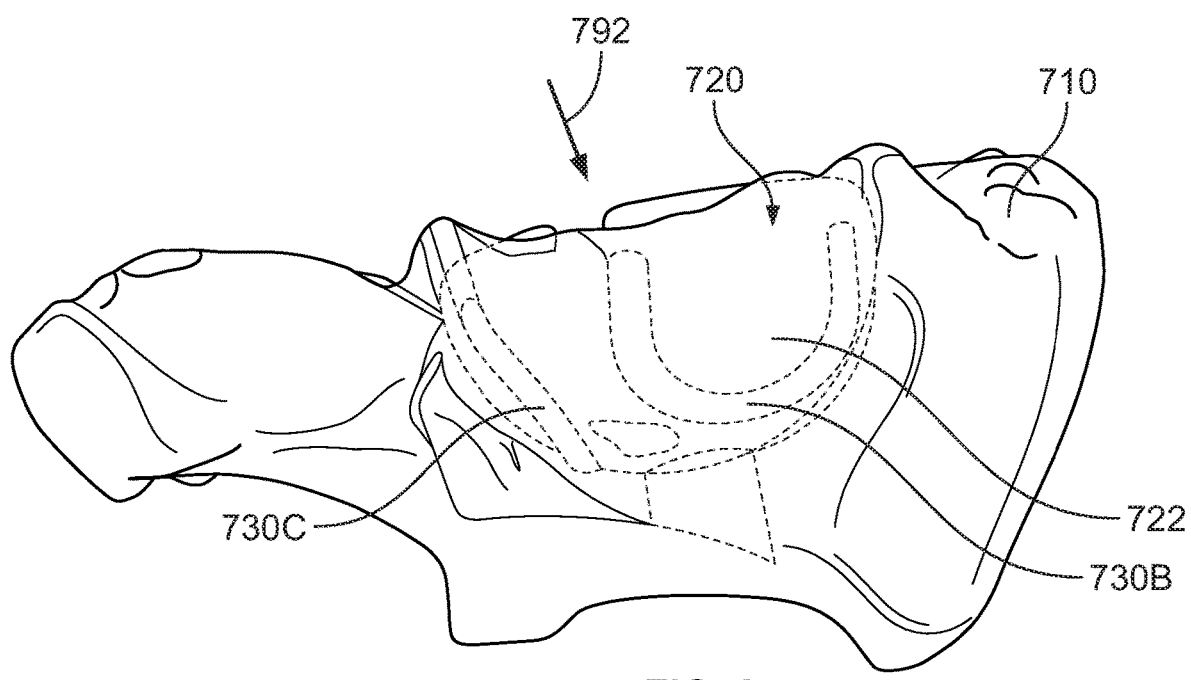

In yet another embodiment, a method of fixation of an acetabular cup to a prepared acetabulum is shown in FIGS. 24 and 25. Unless otherwise stated, like reference numerals refer to like elements of above-described acetabular cup 20, but within the 700-series of numbers. And, unless otherwise stated, the preliminary steps of three dimensional model generation, registration and planning are the same as those described for the implantation of a THA cup described above and shown in FIGS. 14-18. Similarly, the steps for cutting bone in the acetabulum are the same as those described for the THA cup. Although grooves 714A-C in the finished acetabular surface 712 are different from those of acetabulum 12 and 112, the same robot-assisted method may be used to precisely cut such grooves in accordance with a surgical plan. In particular, grooves 714A-C and surface 712 are prepared with bur tool 740 so that acetabular cup 720 may be seated therein.

Turning to insertion of acetabular cup 720 into the acetabular cavity, acetabular cup is first secured to an insertion tool, such as insertion tool 50, and the insertion tool is connected to the robot. With haptic guidance that supplements operation of the robot (not shown), acetabular cup 720 is slip fit into the acetabulum without the need for forced insertion, as indicated by reference numeral 792 in FIG. 25. Because of the precise cuts made into the bone with haptic guidance that follows the surgical plan, protrusions 730A-C of acetabular cup 720 complement grooves 714A-C and advancement of the cup into the cavity is furthered until engagement of the protrusions with respective grooves provides a fixed securement between the cup and the bone when the cup bottoms out within the cavity. Moreover, when such fixation is achieved, outer surface 722 of the cup is flush with the generally hemispherical concave inner surface 712 of the acetabulum.

Advantages of this method include the reduced likelihood that a gap and/or a varying gap will exist between the cup and the acetabulum after fixation of the cup to the bone and also the elimination of the need for an impaction tool. However, it should be noted that impaction is an available option if desired by a user. For example, impaction may be performed where an outer rim of the acetabular cup is stuck on a peripheral bone edge. Other advantages include that the fixation provides locking of the cup in six degrees of freedom rather than fixation limited to a rim region of the cup. Further, the significant surface area contact between the cup and the bone provide greater opportunity for bone ingrowth which also promotes fixation. A similar method of bone preparation and slip fit insertion may be utilized to seat acetabular cups 820, 920, 1020, 1120 and 1220 shown in FIGS. 9-13, respectively. The advantages when performing a method of seating these acetabular cups with other geometries include at least those described for acetabular cup 720 above.

In variations of the method described for fixation of acetabular cup 20, 120, 220, 320, 420, 520, 620, 720, 820, 920, 1020, 1120, 1220, or other acetabular cups contemplated herein, into an acetabulum of a patient, the procedure may be fully automated or may include one or more steps that are fully automated. In these methods, the robot is programmed to perform the applicable steps without physical action by the user. Similar to the semi-autonomous method, the three dimensional model is created and planning for the required bone cuts is performed. However, cutting of the bone and insertion of the cup is done without physical manipulation of the operational tools by a user. In one example, the seating of the acetabular cup into the acetabulum is fully automated by attachment of an end effector of the robot to the handle of the insertion tool that in turn secures the acetabular cup. The robot is controlled to bring the attached cup to the surgical site and to precisely orient the cup and so that it may be seated in the acetabulum in accordance with the surgical plan. Where the cup is adapted for rotational insertion, the robot rotates the handle whereas in a slip fit design the robot pushes the cup into the bone. In some examples, a user of the system may supervise the process and observe the advancement to the fully seated position. For instance, the user may monitor this process through the display of the system or through direct visualization and may intervene as appropriate. In other examples, the user may perform part of the rotational insertion manually. Torque/force sensors may be built into the robot to provide the user with detailed information during the seating process, including the force applied to the cup. Color coding may also be used to provide improved visualization regarding the stages of cup seating.

In some examples, the method is fully automated up until the step of either rotating or slip fitting the acetabular cup to seat it within the acetabular cavity, the latter step optionally performed manually or semi-automatically with haptic guidance. In other examples, the user may interrupt the automated process and intervene to perform one or more steps semi-autonomously. In still other examples, the user may perform some steps of the method with haptic guidance as described above, but not others.

In other variations, certain steps may be performed entirely manually by the user. For example, the initial cut of the acetabular surface to form a bone shape to match an outer surface of the acetabular cup may be done manually with the use of a bur tool. Alternatively, reamer baskets attached to a cutting tool may be used for this initial cutting step. In particular, a series of reamer baskets may be used to cut the majority of the hard bony region until the cut is close to forming a cavity that is the size of the acetabular cup. Then, the bur tool, with haptic guidance provided through the robot, may be used to finish cutting to the required generally hemispherical shape and for cutting the additional grooves in the bone surface so that the bone surface matches the cup. This approach may be described as a hybrid approach because of its use of both manual operation of a tool with reamer baskets and the robotically assisted operation of the bur tool.

In other examples, the rotatable insertion of the cup with angled protrusions may involve the securement of the cup to an insertion tool and then the user, holding a handle of the insertion tool, aligns the protrusions with matching grooves in the acetabular cavity and then turns the handle until the cup bottoms out in the cavity and cannot be advanced further. The grooves in the acetabular surface of the bone function as tracks that assist in guiding the cup into the correct position during advancement. In some examples, the insertion tool may incorporate a torque limiting feature to prevent over torqueing the cup in the acetabular cavity. Torque limiting may also be used in robot assisted methods. Optionally, the three dimensional model along with a marker or tracker on the cup that communicates with the robot may also be used provide visualization for the user to ensure proper placement of the cup as it is rotated into the seated position. This manual approach may also be applied to slip fit acetabular cups by aligning the protrusions with respective grooves in the surface of the acetabulum and then pushing the cup into the cavity to seat it.

In some examples, other tools are used to perform the method of fixation of the acetabular cup to the acetabulum. For instance, a robot with an end effector adapted for securement to the acetabular cup may be used.

In still further examples, the surgical plan for the resection of the acetabulum may be customized and may deviate or otherwise be distinguishable from the geometry of the outer surface of the acetabular cup. For instance the grooves in the bone may not match the protrusions on the cup. This type of approach may be adopted to provide a different type of fixation between the cup and the bone or in some instances may be adopted where it is preferred by the user.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An acetabular cup for implantation into a prepared acetabulum comprising:
   an inner surface;
   an outer surface with a plurality of protrusions projecting outwardly therefrom in predefined locations, wherein the plurality of protrusions are formed monolithically with the outer surface; and
   an end face separating the inner surface and the outer surface, the end face opposite a polar region of the acetabular cup and circumscribing an open end of the acetabular cup,
   wherein a maximum length dimension of a first protrusion of the plurality of protrusions is measured along the outer surface and a maximum depth dimension of the first protrusion is measured in a direction perpendicular to the outer surface, a circumferential component of the maximum length dimension parallel to an edge separating the outer surface from the end face being greater than the maximum depth dimension, wherein the maximum length dimension of the first protrusion extends from a first end portion to a second end portion opposite the first end portion, at least one of the first end portion and the second end portion having a convex surface, the convex surface being convex along the maximum length dimension and in a direction transverse to the maximum length dimension, wherein a central axis passes through an apex of the acetabular cup and a center of a cup opening defined by an inner perimeter of the end face, wherein the maximum length dimension of the first protrusion is oriented at an acute angle relative to a first plane perpendicular to the central axis, the maximum length dimension being longer than any other dimension of the first protrusion, and wherein the acetabular cup is configured to operatively engage to the prepared acetabulum in a planned orientation when the plurality of protrusions are received in corresponding predefined recesses in the prepared acetabulum.

2. The acetabular cup of claim 1, wherein the plurality of protrusions are configured to be received in corresponding predefined recesses having a volume substantially the same as a volume of the plurality of protrusions.

3. The acetabular cup of claim 1, wherein the plurality of protrusions are configured to be received in corresponding predefined recesses having an initial volume less than a volume of the plurality of protrusions.

4. The acetabular cup of claim 1, wherein the plurality of protrusions are configured to snap-fit into the corresponding predefined recesses.

5. The acetabular cup of claim 1, wherein upon rotation of the plurality of protrusions about a polar axis of the acetabular cup, the plurality of protrusions are configured to rotate into engagement with the corresponding predefined recesses.

6. The acetabular cup of claim 1, wherein each protrusion of the plurality of protrusions has a long dimension that is oriented at an acute angle relative to an axis passing through a center of the polar region of the acetabular cup and a center of the open end of the acetabular cup, an end of the long dimension being tapered.

7. The acetabular cup of claim 1, wherein the end face is non-planar.

8. An acetabular cup comprising:
an inner surface;
an outer surface with a plurality of protrusions thereon, each protrusion of the plurality of protrusions having a long dimension with a tapered end that includes a convex surface that is convex along the long dimension and in a direction transverse to the long dimension, the long dimension of a first protrusion of the plurality of protrusions being a maximum dimension of the first protrusion and oriented at an acute angle relative to a first plane, the first plane being perpendicular to a central axis of the acetabular cup that passes through an apex of the acetabular cup in a polar region of the acetabular cup and a center of an open end of the acetabular cup; and
an end face separating the inner surface and the outer surface, the end face opposite the polar region of the acetabular cup and circumscribing the open end of the acetabular cup,
wherein the plurality of protrusions are sized to slidably engage with complementary surfaces in a prepared acetabulum such that when the acetabular cup is rotated into the prepared acetabulum, the plurality of protrusions slide into the complementary surfaces in the prepared acetabulum.

9. The acetabular cup of claim 8, wherein the taper of each protrusion of the plurality of protrusions is at a leading end of the long dimension, the leading end located further from the end face than other locations on the protrusion.

10. The acetabular cup of claim 8, wherein each protrusion of the plurality of protrusions includes a combination of flat and convex surfaces.

11. The acetabular cup of claim 8, wherein the plurality of protrusions include a second protrusion and a third protrusion, and each of the first, second and third protrusions is located at a first distance from the end face and equally spaced around a perimeter of the outer surface at the first distance.

12. The acetabular cup of claim 8, wherein the long dimension of each protrusion of the plurality of protrusions extends between a leading end and a trailing end, the leading end and the trailing end both being defined by a rounded taper.

13. The acetabular cup of claim 8, wherein the tapered end of the long dimension of each protrusion of the plurality of protrusions is a leading end and the long dimension extends between the leading end and a trailing end, a width of the protrusion tapering continuously from the trailing end to the leading end.

* * * * *